United States Patent
Kalra

(10) Patent No.: US 8,968,675 B2
(45) Date of Patent: Mar. 3, 2015

(54) SAMPLE PROCESSING SYSTEM

(71) Applicant: Biogenex Laboratories Inc., San Ramon, CA (US)

(72) Inventor: Krishan L. Kalra, Danville, CA (US)

(73) Assignee: Biogenex Laboratories Inc., San Ramon, CA (US)

( * ) Notice: Subject to any disclaimer, the term of this patent is extended or adjusted under 35 U.S.C. 154(b) by 0 days.

(21) Appl. No.: 13/926,216

(22) Filed: Jun. 25, 2013

(65) Prior Publication Data

US 2013/0338045 A1    Dec. 19, 2013

Related U.S. Application Data

(63) Continuation of application No. 12/542,646, filed on Aug. 17, 2009, which is a continuation-in-part of application No. 11/373,758, filed on Mar. 9, 2006, now abandoned.

(51) Int. Cl.
| | |
|---|---|
| G01N 33/00 | (2006.01) |
| G01N 1/28 | (2006.01) |
| B01L 3/00 | (2006.01) |
| G01N 1/31 | (2006.01) |
| B01L 7/00 | (2006.01) |
| G01N 35/00 | (2006.01) |
| G01N 35/10 | (2006.01) |

(52) U.S. Cl.
CPC . *G01N 1/28* (2013.01); *B01L 3/508* (2013.01); *G01N 1/312* (2013.01); *B01L 3/5085* (2013.01); *B01L 7/52* (2013.01); *B01L 2200/0689* (2013.01); *B01L 2200/147* (2013.01); *B01L 2300/022* (2013.01); *B01L 2300/024* (2013.01); *B01L 2300/041* (2013.01); *B01L 2300/0822* (2013.01); *G01N 35/0099* (2013.01); *G01N 35/109* (2013.01); *G01N 2001/317* (2013.01); *G01N 2035/00752* (2013.01)
USPC ............... 422/402; 422/68.1; 422/82.12

(58) Field of Classification Search
USPC ................... 422/402, 68.1, 82.12
See application file for complete search history.

(56) References Cited

U.S. PATENT DOCUMENTS

| | | |
|---|---|---|
| 3,833,449 A | 9/1974 | Johnson |
| 3,972,423 A | 8/1976 | Tipton |
| 4,033,809 A | 7/1977 | Tipton |
| 4,455,188 A | 6/1984 | Stormby |

(Continued)

FOREIGN PATENT DOCUMENTS

| | | |
|---|---|---|
| JP | 1-248060 | 10/1989 |
| JP | 07-113731 | 5/1995 |

(Continued)

OTHER PUBLICATIONS

Japanese First Office Action with translation dated Jul. 14, 2009.

*Primary Examiner* — Sam P Siefke
(74) *Attorney, Agent, or Firm* — Knobbe, Martens, Olson & Bear, LLP

(57) ABSTRACT

In accordance with an embodiment of a system for handling and processing chemical and/or biological samples, a Micro-Chamber comprises a substrate, a reservoir formed on the substrate for receiving a chemical and/or biological sample, and an encoder such as a barcode or other suitable device. The encoder encodes information describing at least one characteristic of the substrate and/or reservoir.

14 Claims, 35 Drawing Sheets

(56) References Cited

U.S. PATENT DOCUMENTS

| | | |
|---|---|---|
| 5,090,242 A | 2/1992 | Hilton |
| 5,207,251 A | 5/1993 | Cooks |
| 5,316,181 A | 5/1994 | Burch |
| 5,439,649 A | 8/1995 | Tseung et al. |
| 5,563,584 A | 10/1996 | Rader et al. |
| 5,580,414 A | 12/1996 | Ljungmann |
| 5,580,524 A | 12/1996 | Forrest et al. |
| 5,645,798 A | 7/1997 | Schreiber et al. |
| 5,839,091 A | 11/1998 | Rhett et al. |
| 5,948,359 A | 9/1999 | Kalra et al. |
| 6,032,529 A | 3/2000 | Saito et al. |
| 6,180,061 B1 | 1/2001 | Bogen et al. |
| 6,183,693 B1 | 2/2001 | Bogen et al. |
| 6,296,809 B1 | 10/2001 | Richards et al. |
| 6,403,931 B1 | 6/2002 | Showalter et al. |
| 6,428,752 B1 | 8/2002 | Montagu |
| 6,495,106 B1 | 12/2002 | Kalra et al. |
| 6,541,261 B1 | 4/2003 | Bogen et al. |
| 6,626,224 B1 | 9/2003 | Ljungmann |
| 6,660,527 B2 | 12/2003 | Stroup |
| 2002/0132344 A1 | 9/2002 | Wangh |
| 2003/0044837 A1 | 3/2003 | Schermer et al. |
| 2003/0216974 A1 | 11/2003 | Browne |
| 2004/0131505 A1 | 7/2004 | Koeda |

FOREIGN PATENT DOCUMENTS

| | | |
|---|---|---|
| JP | 9-210881 | 8/1997 |
| JP | 2001-133464 | 5/2001 |
| WO | WO 99/44030 | 9/1999 |
| WO | WO 01/07890 | 2/2001 |
| WO | WO 01/23091 | 4/2001 |
| WO | WO 01/51909 | 7/2001 |

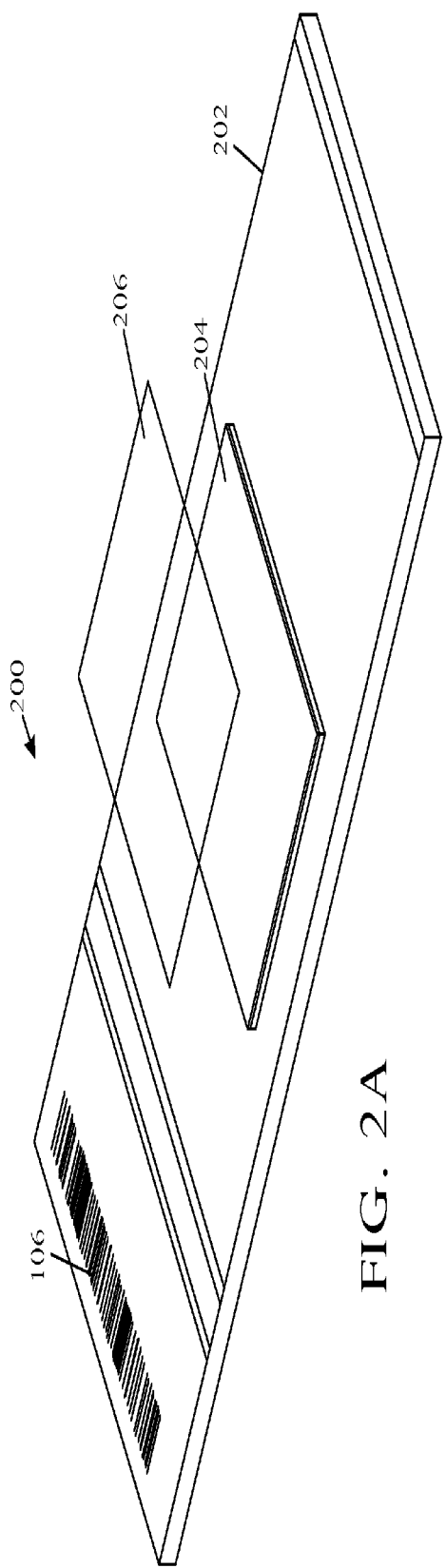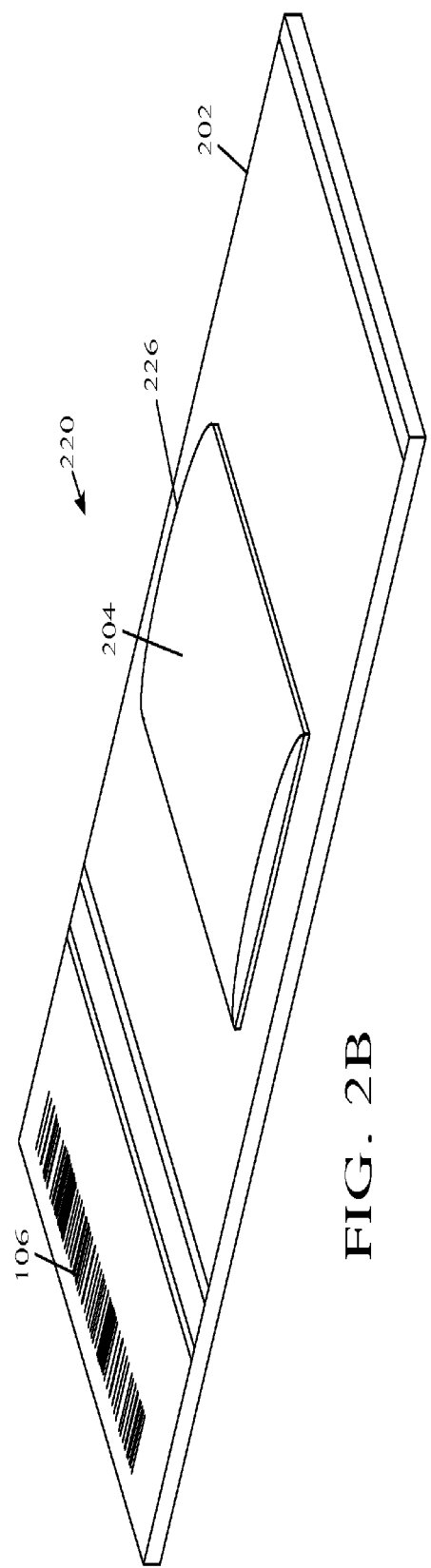
FIG. 2A
FIG. 2B

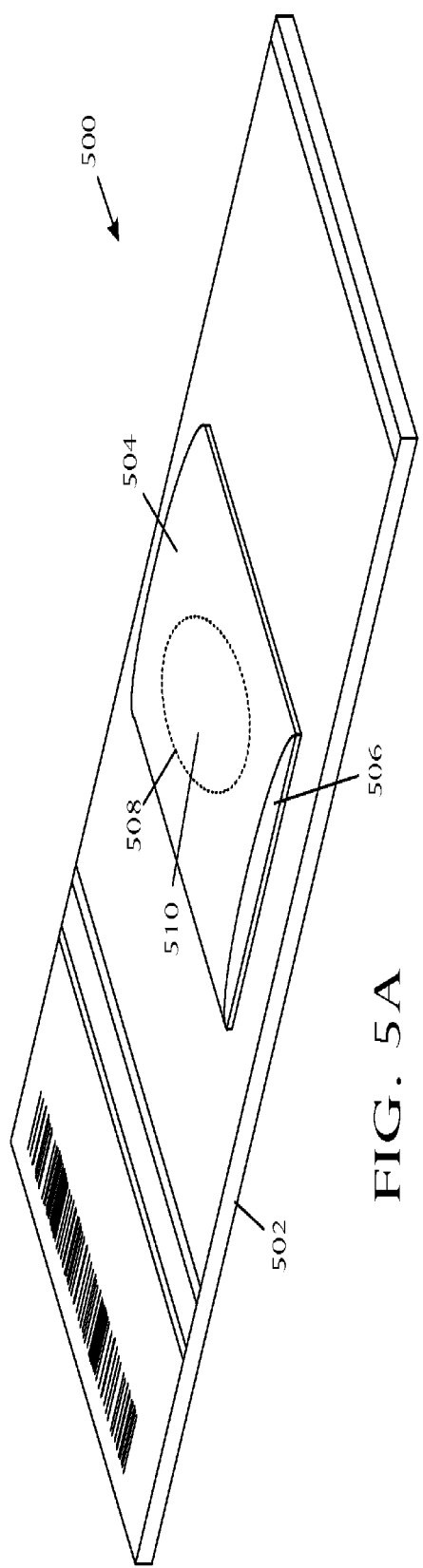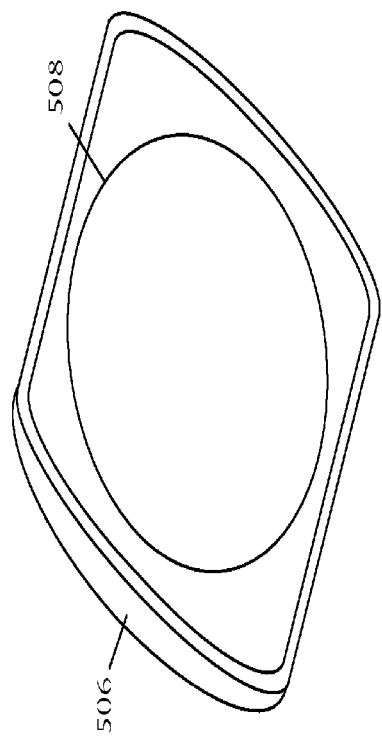
FIG. 5A
FIG. 5B

SAMPLE PROCESSING SYSTEM

REFERENCE TO RELATED APPLICATIONS

The present application is a continuation of U.S. application Ser. No. 12/542,646 filed Aug. 17, 2009, which is a continuation-in-part of U.S. application Ser. No. 11/373,758 filed Mar. 9, 2006. Each of the priority applications is hereby incorporated by reference in its entirety.

BACKGROUND OF THE INVENTION

Over the past decade, researchers have developed molecular technologies for disease diagnoses that analyze proteins and DNA/RNA messages that encode them. These developments have facilitated new insights into the causes of disease and into the early detection of diseases and the accompanying potential therapeutic response. Through genomics, scientists have determined that chromosomal and genetic abnormalities are fundamental sources of human disease. Chromosomal and genetic abnormalities encompass a broad range of irregularities, including numerical and structural changes in chromosomes, amplifications and deletions of genes, as well as mutations within specific gene sequences. Scientific evidence suggests that these chromosomal changes are integral to cancer progression and are the most significant markers of cancer detection. Molecular diagnostic laboratories have long used archaic, manual, and cumbersome techniques that often lead to poorly reproducible and inaccurate results. Even today, most molecular and cell-based diagnostic systems use outdated and non-integrated technologies unable to cost-effectively perform massively parallel-scale analyses. System capabilities are further stressed by the genomics revolution that has accelerated demand for potential markers for use in target validation in drug discovery and development. Consequently, additional automation and parallelism are sought to enable efficient specimen handling, processing and analysis.

SUMMARY

In accordance with an embodiment of a system for handling and processing chemical and/or biological samples, a MicroChamber comprises a substrate, a reservoir formed on the substrate for receiving a chemical and/or biological sample, and an encoder such as a barcode or other suitable device. The encoder encodes information describing at least one characteristic of the substrate and/or reservoir.

BRIEF DESCRIPTION OF THE DRAWINGS

Embodiments of the invention relating to both structure and method of operation, may best be understood by referring to the following description and accompanying drawings whereby:

FIGS. 2A-2C are perspective pictorial diagrams illustrating various embodiments of a MicroChamber including a MicroChamber cover;

FIGS. 5A and 5B are perspective pictorial diagrams showing an embodiment of MicroChamber with a cover that includes a vesicle for dispensing liquid to the microenvironment within the MicroChamber;

DETAILED DESCRIPTION

To solve the challenges of the post-genomic era and to accelerate clinical diagnostics and drug discovery development, embodiments of a sample processing system that automates processing of a sample, such as a chemical and/or biological sample, are disclosed. The sample processing system enables total walk-away, industrial scale, streamlined, and standardized sample processing and testing for multiple samples simultaneously in applications such as DNA microarrays, protein microarrays, Fluorescence In Situ Hybridization (FISH), In Situ Hybridization (ISH) assays, Immunohistochemistry (IHC) samples, staining, and image analysis.

Sample processing systems disclosed herein can perform functions such as (a) individual slide temperature control, (b) dispensing a wide range of reagent volumes from nanoliters (vl) to multiple milliliters (ml), (c) microtiter plate capabilities for small volume reagents, (d) automated placement and removal of reservoir covers and cover slips, (e) walk-away automation with minimal user intervention, (f) barcode and Radio Frequency Identification (RFID) tracking for protocols, reagents, and slides among multiple sample processing systems, (g) independent, environmentally-controlled processing for multiple slides or substrates, (h) reagent temperature control, (i) over-temperature protection and control, (j) liquid level sensing in a reagent/probe container, (k) usage of disposable pipette tips in a range of sizes for dispensing variable quantities of substances, and (l) centralized user interface to one or more sample processing systems. The sample processing systems can also provide capability to process deoxyribonucleic acid (DNA) and protein microchips, and the capability to process multiple samples using different protocols simultaneously, such as tissue arrays, Fluorescence In Situ Hybridization (FISH), In Situ Hybridization (ISH) assays, and Immunohistochemistry (IHC) samples.

The sample processing system can also be configured to create a MicroChamber in which any suitable process can be performed, such as chemical, biological, genomics, proteomics, histology, and/or cytology assays below, at, and/or above room temperature and humidity, thereby creating an enclosed microenvironment for sample processing.

Other features of the system enable automatically separating toxic waste from nontoxic waste; loading and unloading slides; and prioritizing slide processing.

Figure 1A:
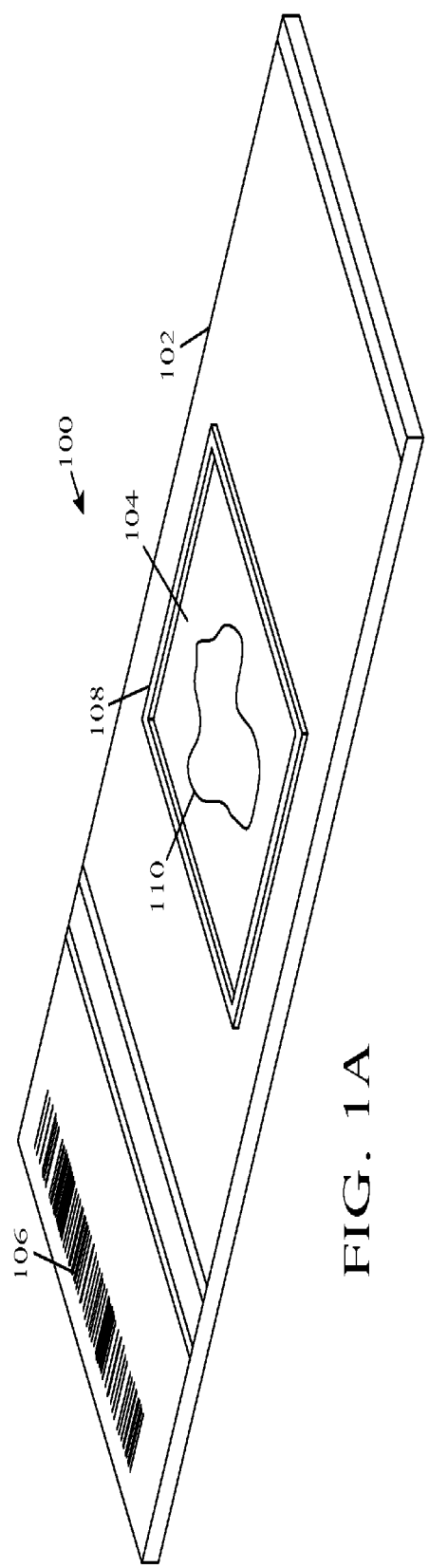
FIGS. 1A-1D are perspective pictorial diagrams illustrating various embodiments of a substrate, such as a slide, forming part of a MicroChamber.

Referring to FIG. 1A, an embodiment of a MicroChamber 100 is shown that includes a substrate 102, a reservoir 104 formed on the substrate 102 for receiving one or more reagents and/or a sample 110, such as a chemical and/or biological sample, and a barcode 106. An encoder, such as barcode 106 can be formed on the substrate 102 to encode information describing at least one characteristic of the substrate 102 and/or the reservoir 104. Note that other suitable encoder devices can be used in addition to, or instead of, the barcode 106.

A sample processing system can be configured to scan barcodes 106 to identify various characteristics of MicroChamber 100. In some embodiments, the barcode 106 encodes any suitable information such as reservoir volume, reservoir size, reservoir shape, reservoir depth, number of reservoirs, substrate material, substrate electrical characteristics, substrate color, presence and/or properties of components attached to the substrate, and/or sample type, among other items.

The reservoir 104 can be constructed using a barrier 108 formed on a substrate 102. The barrier 108 has a shape, size, and height selected to contain a specified area or volume. In some embodiments, the barrier 108 can be formed on a substrate or slide that holds a pre-applied sample 110, however, the barrier 108 can be formed on the substrate 102 before or after application of the sample. Any suitable material or substance can be used to form the barrier 108, such as epoxy, a wax film (e.g., Parafilm™), Teflon™, and/or oil. The barrier 108 may be applied using any suitable method, such as adhesive tape, annealing, ink (e.g., Teflon™ ink), paint, and/or deposition. In some embodiments, the barrier 108 can be constructed from a hydrophobic material or substance to contain hydrous as well as anhydrous substance(s) within the reservoir 104. In some embodiments, the barcode 106 may include information regarding the size of the barrier 108, and/or a sealing device or sealing agent that is used to create the barrier 108 around the reservoir 104.

The reservoir 102 and barrier 108 can be configured to reduce or even eliminate air bubbles in reservoir 102 when the reservoir 102 is covered to form an enclosed microenvironment. Such a configuration can also reduce the volume of reagent used in a process or application, as well as evenly distribute substances in reservoir 102.

Figure 1B:
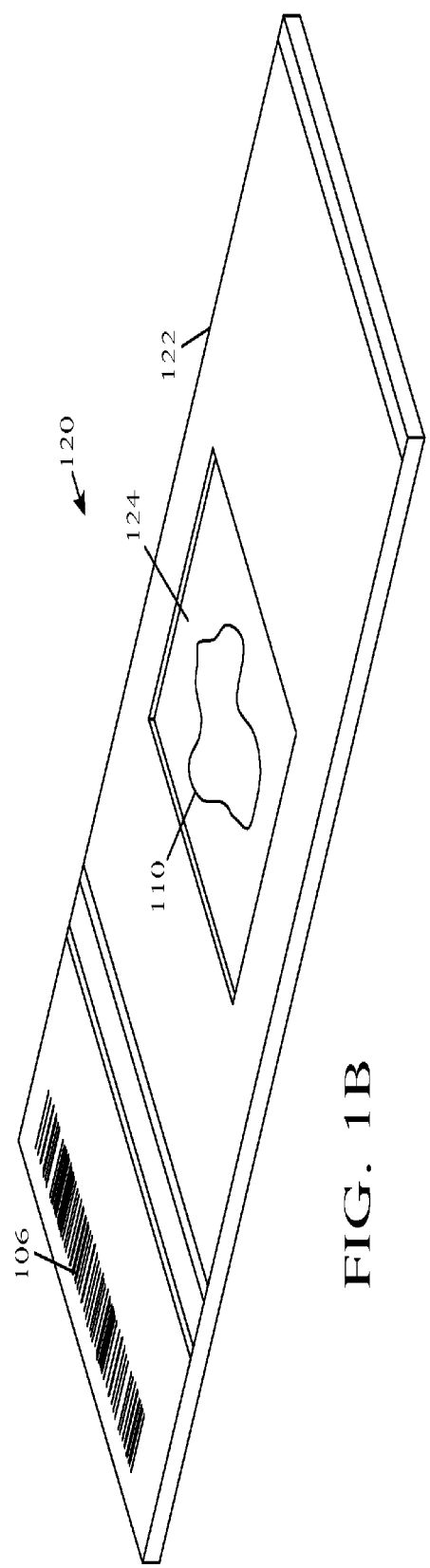

Referring to FIG. 1B, another embodiment of a MicroChamber 120 is shown in which a barrier 108 around the reservoir 124 is formed as a depression in the substrate 122. The shape, size, and depth of the reservoir 124 can be selected to contain a specified volume. Programmed control of barrier deposition speed can be implemented to enable deposition of different materials with various flow rates and solidification times and determine barrier thickness based on the viscosity of the substance used to create the barrier 108.

Figure 1C:
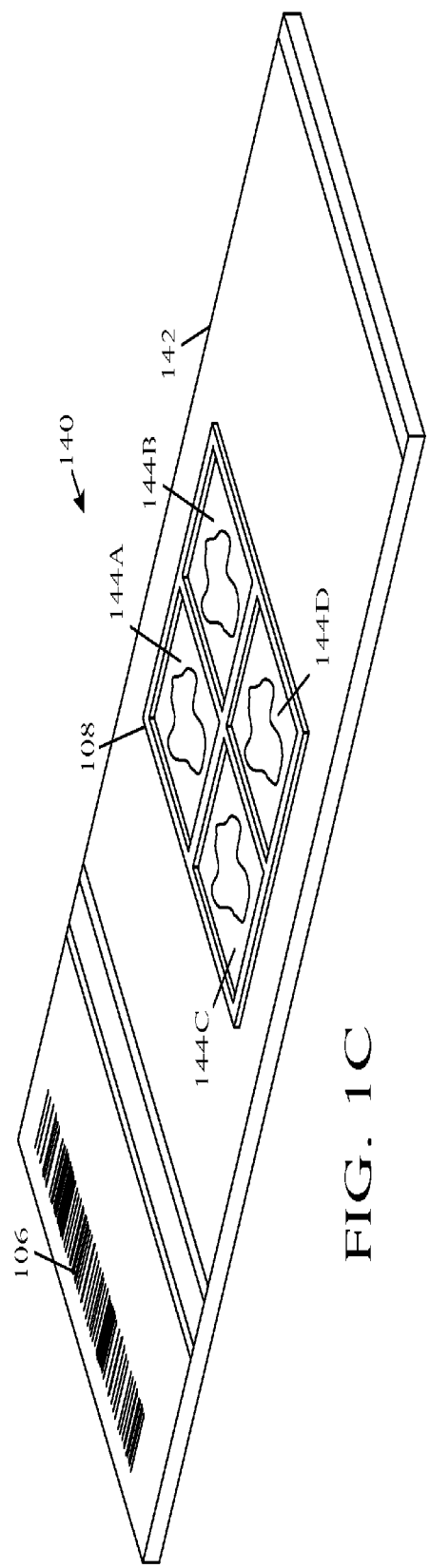
Figure 1D:
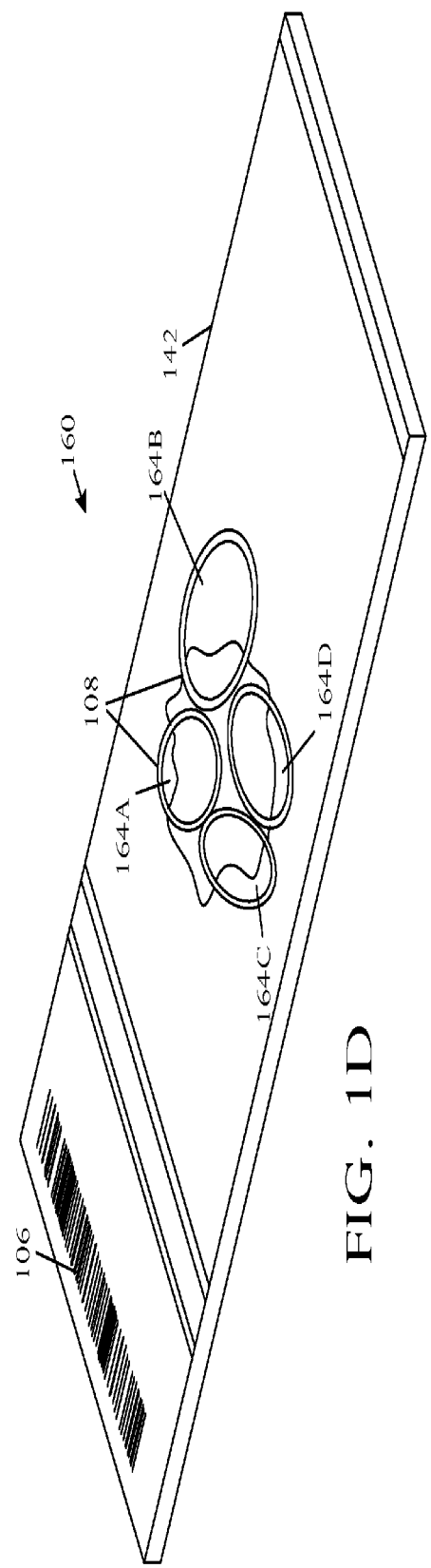

Referring to FIG. 1C, an embodiment of another MicroChamber 140 is shown that includes a plurality of reservoirs 144A-D formed on the substrate 142 to accommodate a sample, such as a chemical and/or biological sample. The reservoirs 144A-D are depicted with the same shape, size, and depth and containing the same volume. In other embodiments, for example as shown in FIG. 1D, reservoirs 164A-F may vary in shape, size, depth, and/or volume.

In various embodiments, the substrate 102, 122, 142, 162 may be formed from glass, for example a glass dish, slide, microscope slide, bowl, or the like. Other suitable substrate materials can be used, such as thermally-conductive materials, electrically conductive or nonconductive materials, piezo-electric materials, silicon materials, polymer materials, and others.

Referring to FIG. 2A, an embodiment of a MicroChamber 200 is shown including a substrate 202, a reservoir 204, and a cover 206 that can be positioned on substrate 202 to enclose reservoir 204 and form a microenvironment for processing the sample. The cover 206 can be any suitable device, such as a cover slip, with a size and shape configured to cover the periphery of reservoir 204 and/or the barrier 108 (FIG. 1A). In another embodiment of a MicroChamber 220, for example as shown in FIG. 2B, the cover 226 can be a cap that is configured to enclose the reservoir 204. In various embodiments, the cover 206, 226 is constructed from any suitable material, such as glass, plastic, hard plastic, polymer, and/or one or more layers, such as layers formed from solidified or dried layers of a substance.

Figure 2C:
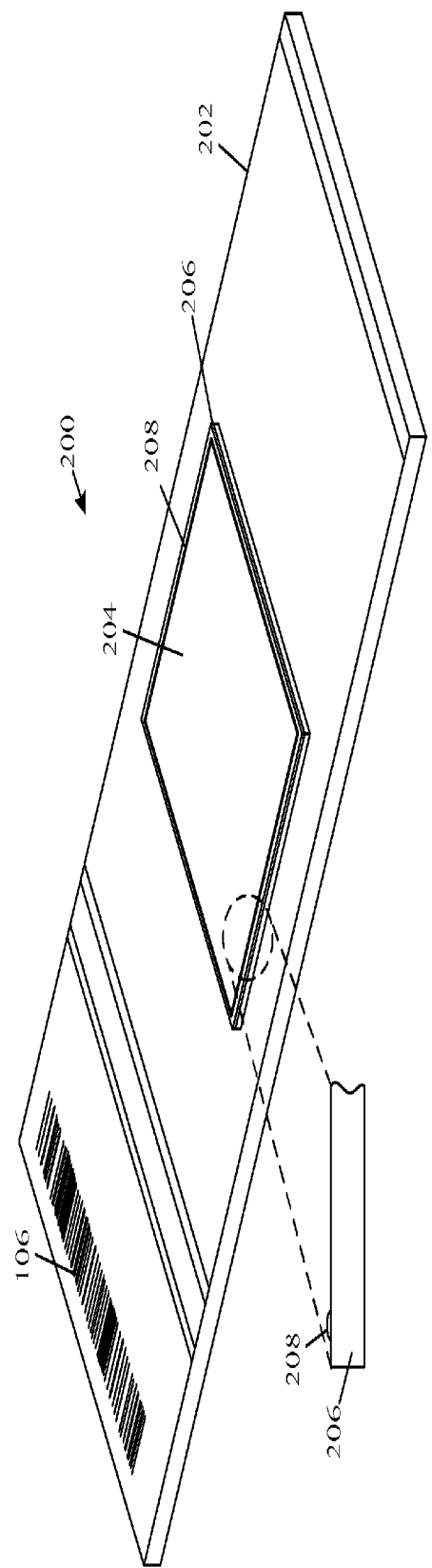

FIG. 2C shows an embodiment of the MicroChamber 200 that further includes a coating 208 formed on a cover 206, the figure also depicting an insert showing a magnified view of the cover 206 with coating 208 around the edge of cover 206. The coating 208 can be used to help preventing adjacent covers 206 from adhering to one another, and can be any suitable material or substance, such as paint, metal, powder, lamination, foil, and the like. The coating 208 can be applied in any suitable location on cover 206 and can have properties that allow the position and orientation of cover 206 to be detected automatically. For example, the coating 208 can have conductive properties that allow the coating 208 to be detected electronically, and/or optical properties that allow the coating to be detected with optical sensors. In some embodiments, the position and orientation of cover 206 can be determined when the coating 208 is applied in a recognizable pattern around one or more portions of the periphery or other suitable location on cover 208. The coating 208 can also be configured to form at least a portion of barrier 108 (FIG. 1A) in some embodiments. A signal processing system (not shown) can be configured to determine the position and orientation of the cover 206 based on sensor signals. The sample processing system can use the position and orientation information to locate and position the cover(s) 206 as desired.

Figure 3:
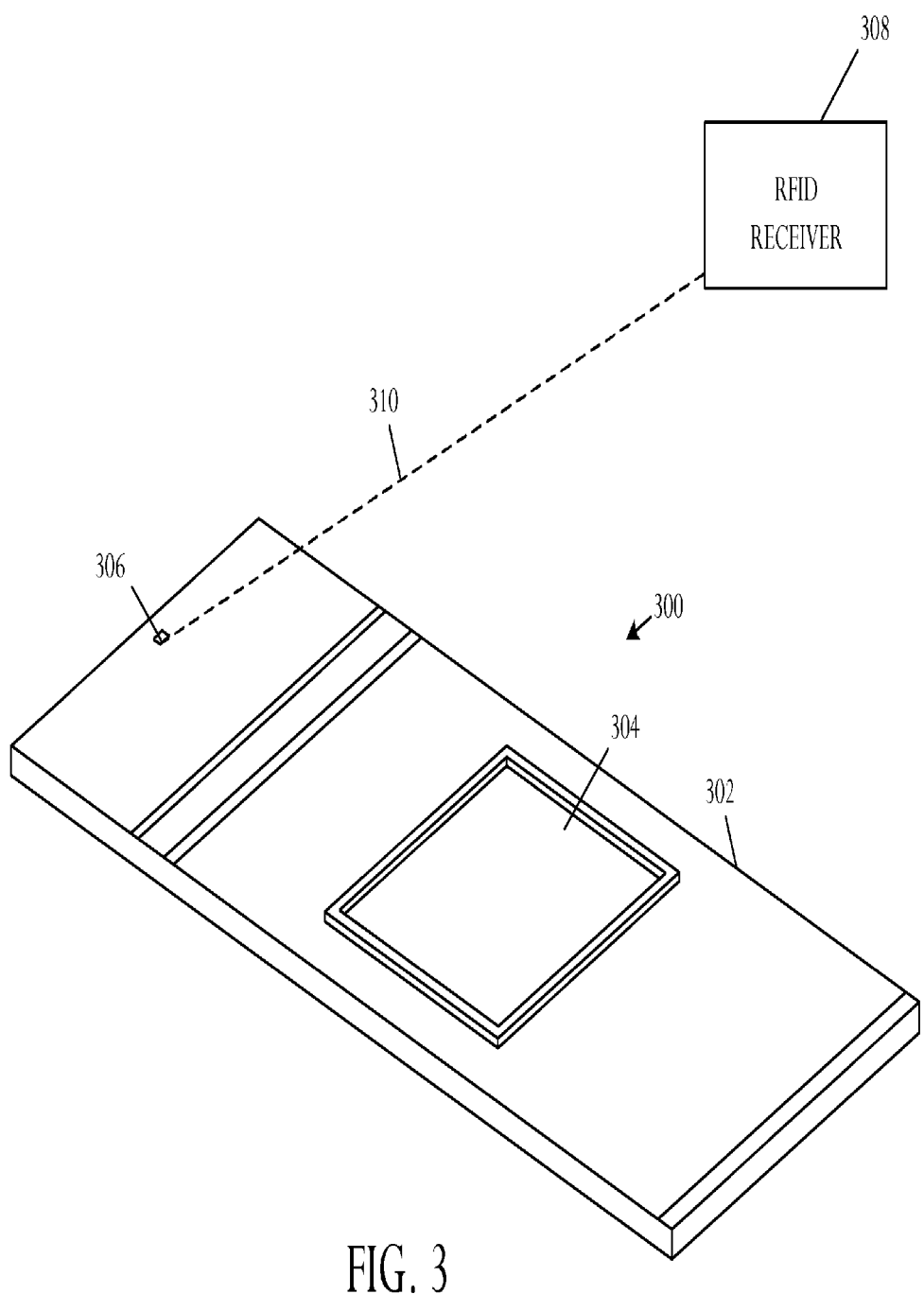
FIG. 3 is a perspective pictorial diagram that shows an embodiment of a substrate labeled using a radio frequency identifier.

Referring to FIG. 3, an embodiment of another MicroChamber 300 is shown that includes a substrate 302, a reservoir 304 formed on the substrate 302 that can receive a sample, such as a chemical and/or biological sample, and a radio frequency identification tag (RFID) 306. The term RFID describes the use of radio frequency signals to provide information regarding the identity, location, and other characterizing information about MicroChamber 300. The RFID tag 306 coupled to the substrate 302 can transmit RF signals 310 that include information describing at least one characteristic of the substrate 302 and/or reservoir 304. For example, the RFID tag 306 may encode at least one information item such as a unique identifier for the MicroChamber 300, reservoir volume, reservoir size, reservoir shape, reservoir depth, number of reservoirs, substrate material, substrate electrical characteristics, substrate color, characteristics of the barrier 108 (FIG. 1A), and the presence and/or properties of components and samples attached to and mounted on the substrate 302. An RFID receiver 308 in the transmitting range of RFID tag 306 can detect signals 310 transmitted by RFID tag 306 and use the information in a processing system that tracks any suitable aspects of MicroChamber 300, such as inventory, configuration, location, and current state of usage of the MicroChamber 300.

Figure 4:
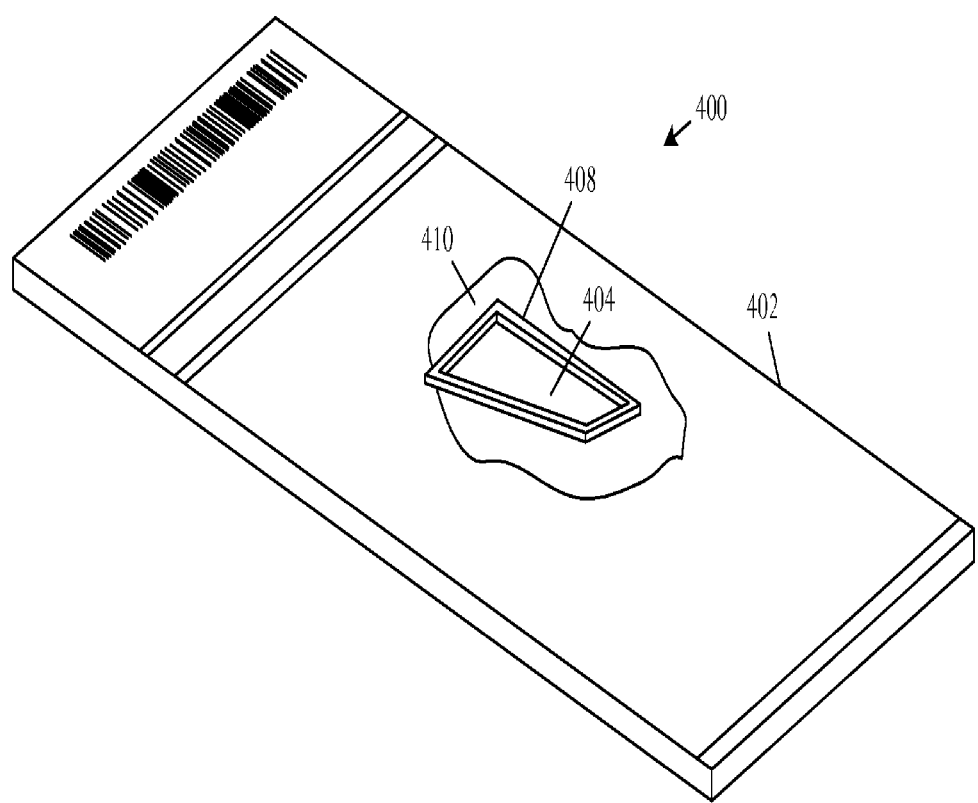
FIG. 4 is a perspective pictorial diagram depicting an embodiment of a substrate with a barrier formed by a sample processing system.

Referring to FIG. 4, a MicroChamber 400 is shown that comprises a substrate 402, a barrier 408, and a reservoir 404 enclosed by the barrier 408. A sample 410 can be applied to the substrate 402 before the substrate 402 is inserted or placed into the sample processing system for handling. The barrier 408 can be constructed to a selected shape, size, and height selected to contain a specified volume. As a result, a portion of a pre-applied sample 410 may lie outside barrier 408. Alternatively, the barrier 408 can be formed on the substrate 402 around the pre-applied chemical and/or biological sample 410 with the barrier position, size, shape, thickness and/or volume controlled by the sample processing system. The characteristics of the barrier 408 can also be controlled by the user according to directions and commands received via a user interface to form one or more reservoirs corresponding to one or more regions of interest in the chemical and/or biological sample.

The sample processing system can be controlled to produce a single barrier 408 and single reservoir 404, or multiple barriers and corresponding multiple reservoirs having the same or different shapes and sizes. In some embodiments, double barriers 408 are used. Sealant can be placed in between the double barrier or outside or inside of the barriers. A sealing device or sealing agent can be used between the double barriers 408, and/or inside or outside of the barriers 408.

Referring to FIG. 5A, an embodiment of a MicroChamber 500 is shown comprising a substrate 502, a reservoir 504 formed on the substrate 502, a cover 506 that can be secured to the substrate 502 to contain the reservoir 504, and a vesicle 508. The vesicle 508 can be attached to or integrally formed with the cover 506 and contains a substance, such as a reagent.

FIG. 5B shows a view of the vesicle 508 in the cover 506, with the cover 506 being adapted to contain substances. The vesicle 508 is constructed to securely contain a specified volume of substance such as a reagent until application of the substance to a sample is desired. The vesicle 508 can be further adapted to be opened or breached at a suitable time to enable application of the substance in the vesicle 508 to the sample. For example, in some embodiments, the vesicle 508 can be dissolvable when contact is made with substance(s) in the reservoir 504. The vesicle 508 may be configured to rupture upon contact with the substrate 502. In another example, a sharp surface may be formed on the substrate or the cover that cuts a portion of the vesicle 508 when the cover 506 is placed on the substrate 502. In some embodiments, the vesicle 508 can be constructed of a material that dissolves upon chemically reacting with substance(s) in the reservoir 504, upon reaching a specified temperature, or other suitable method. In other embodiments, the cover 506 can be coated with a substance that combines with substances in the reservoir 504 when the cover 506 is positioned on the reservoir 504.

The covers 206, 226, 506 can have different shapes, sizes, color, opacity, or other specified characteristics, depending on the requirements for the sample processing system. For example, some processes may require exposing the contents of the reservoir 204, 304, 404, 504 to light having a specified wavelength. Some of the covers can be configured as a filter to allow light of the specified wavelength to reach the contents of the reservoir 204, 304, 404, 504. Further, the covers 206, 226, 506 can be changed during a process, for example, when a cover having a particular characteristic is required during a particular phase of the process but is not suitable for other phases of the process. The covers 206, 226, 506 can be any suitable material, and can further be laminated, disposable, reusable, washable, and/or dryable.

Figure 6A:
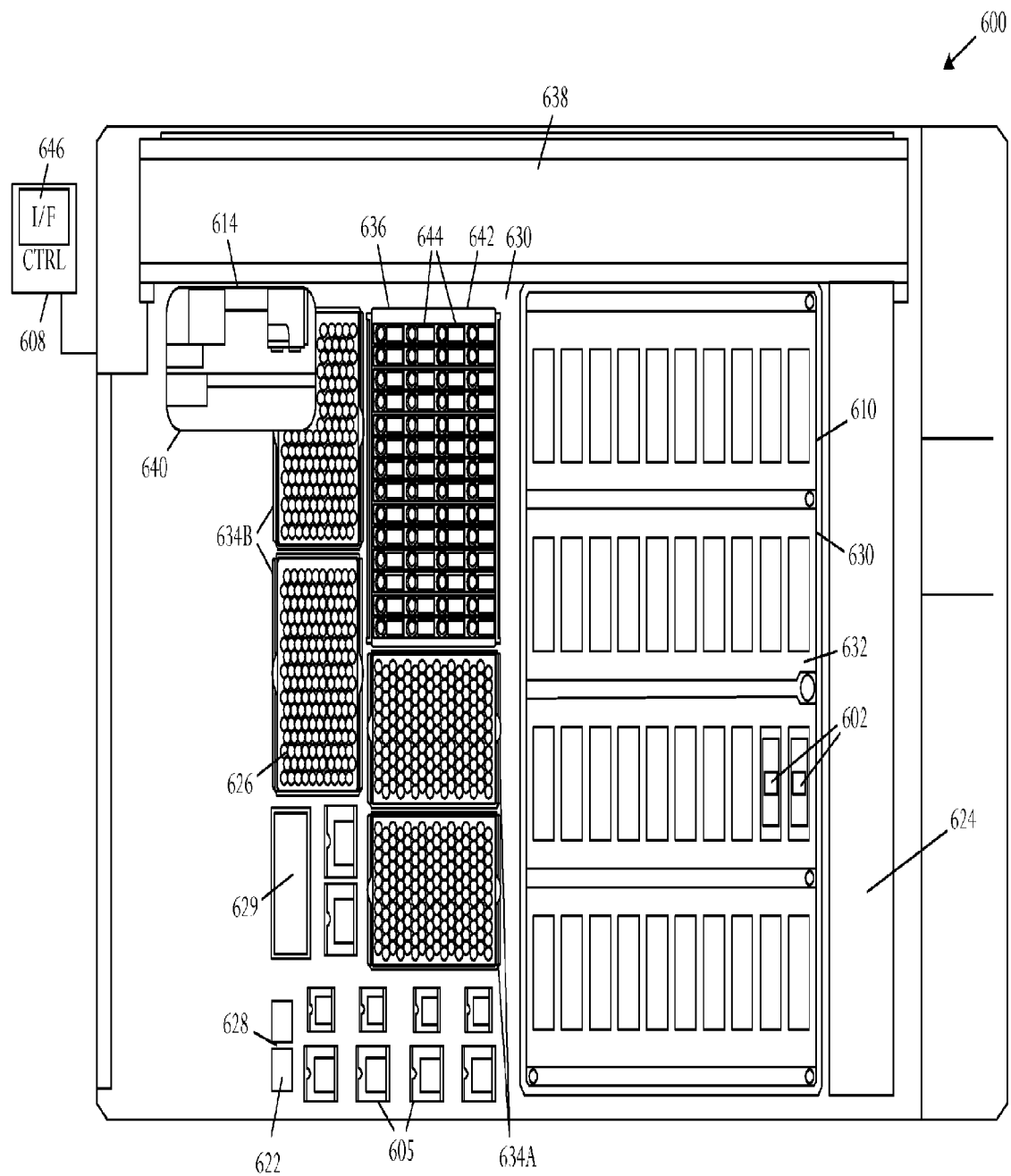
FIGS. 6A-6E show multiple views of an embodiment of a sample processing system that is adapted to concurrently and individually control processing of a plurality of samples.
Figure 6B:
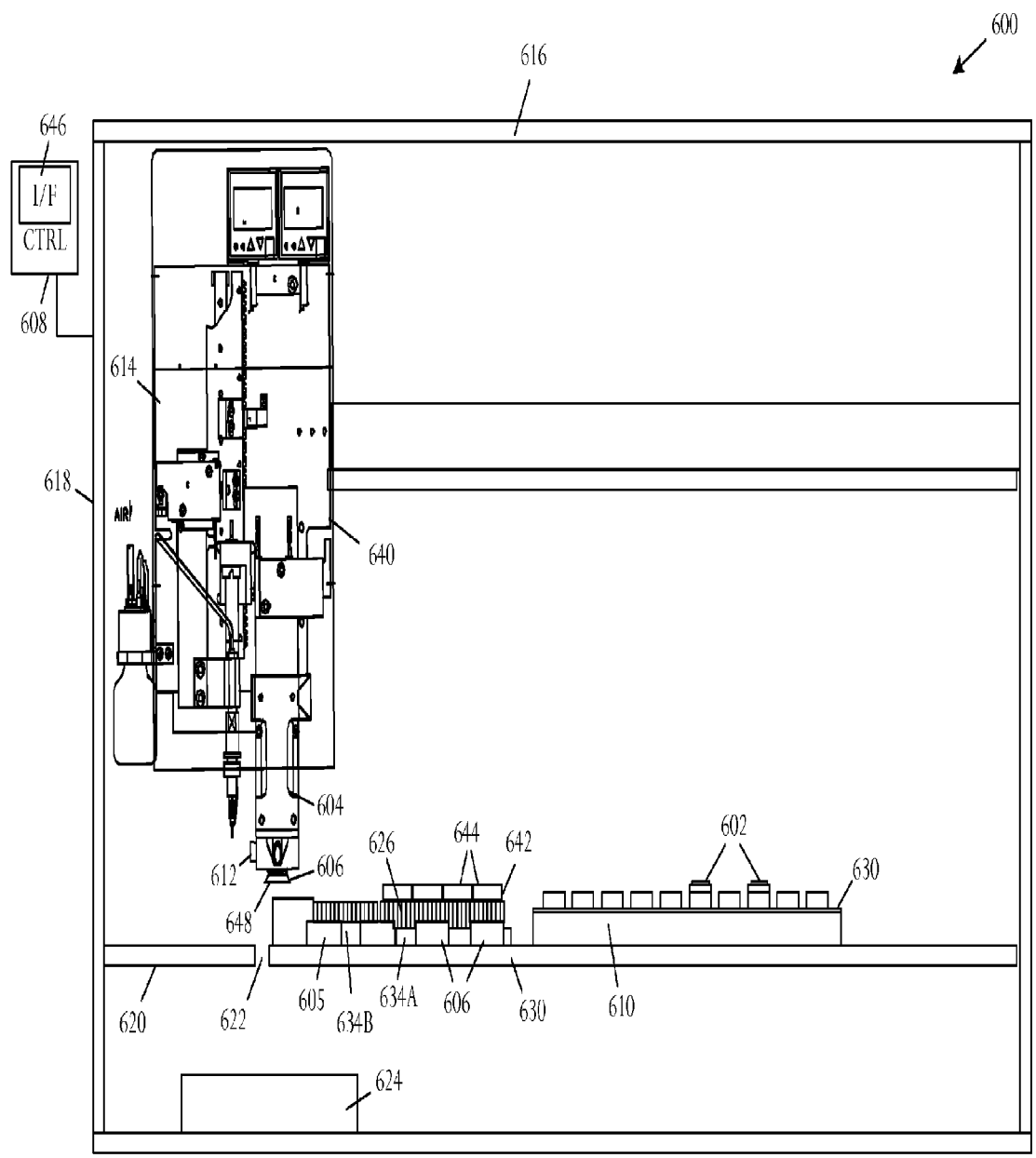
Figure 6C:
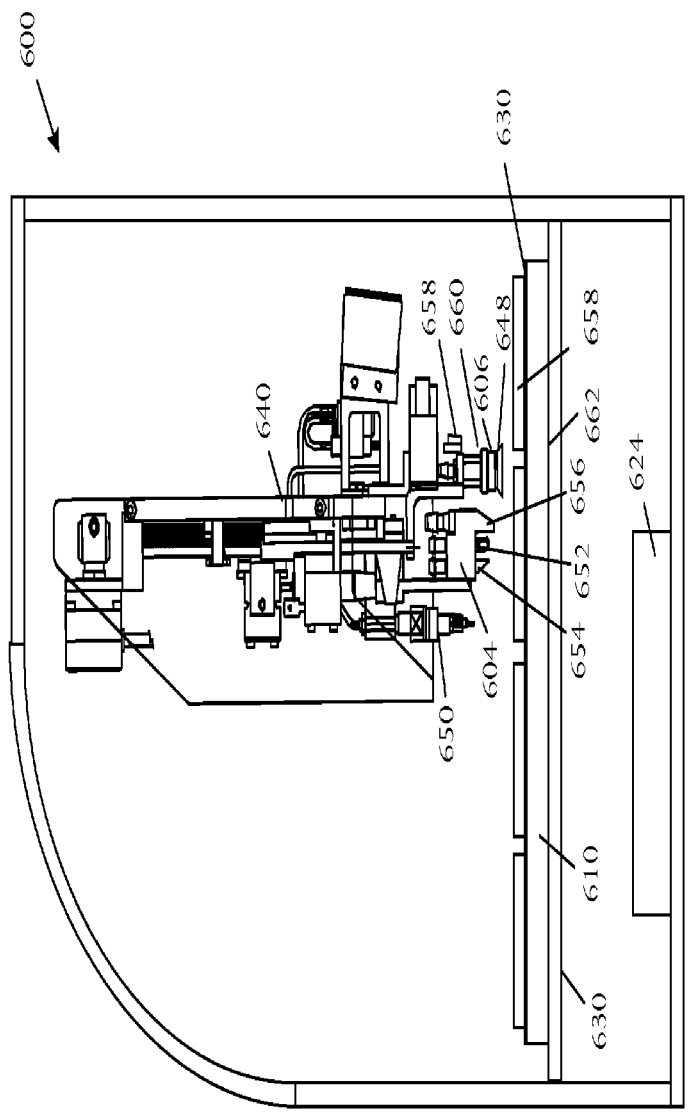
Figure 6D:
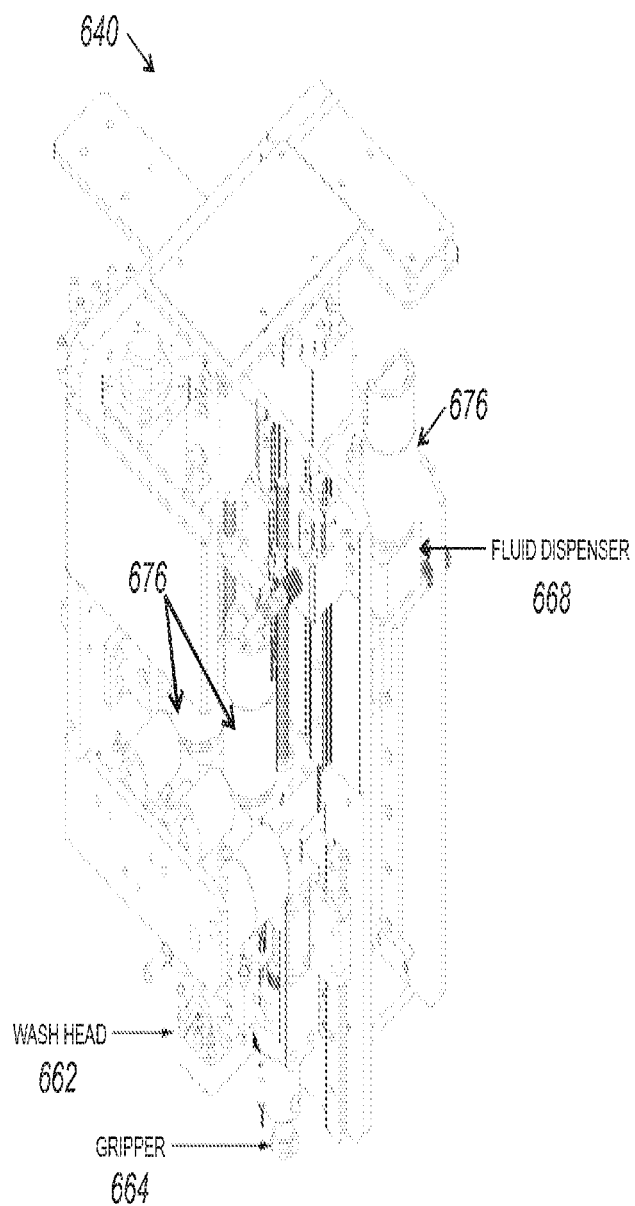
Figure 6E:
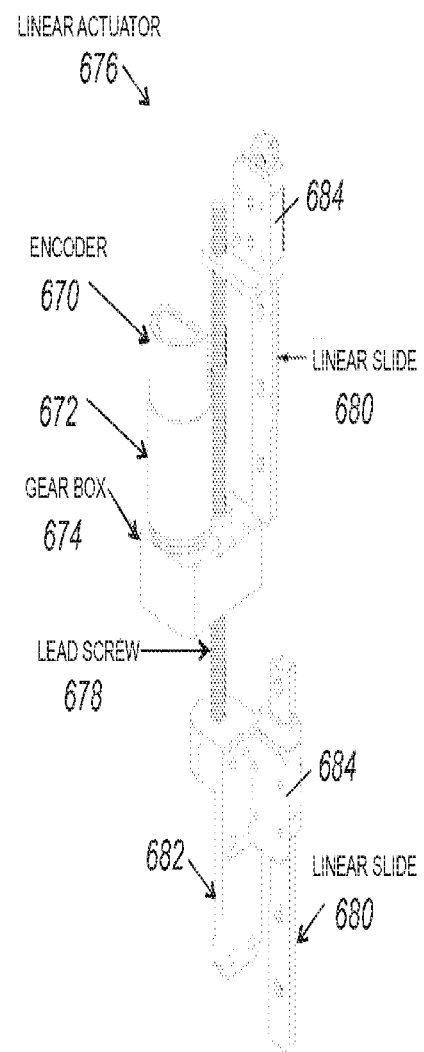

Referring to FIGS. 6A-6C, multiple views of a sample processing system 600 that is adapted to concurrently and individually control processing of a plurality of samples is shown. The illustrative sample processing system 600 is a self-contained, automated system with cover placement and removal capabilities, precision aspirating and dispensing of reagents, and individual temperature control for MicroChambers 602.

In some embodiments, sample processing system 600 includes a platform 630 and rack 642 that can be held by the platform 630 or coupled to the platform 630 and adapted to hold multiple reagent containers 644. The rack 642 can also be configured with one or more individually controllable heating elements to maintain the reagents at different selected temperatures. The sample processing system 600 can also be configured to independently maintain a plurality of MicroChambers, such as MicroChamber 200 in FIG. 2C, at different environmental conditions, such as different temperature, light, and/or humidity levels.

In some embodiments, the robotic device 640 is mounted on a movable arm 614 that can be positioned in one, two, and/or three dimensions relative to the platform 630. The robotic device 640 can be configured to accept different types of attachments to perform various different operations and functions, such as gripping and releasing covers; positioning and removing a cover from a reservoir, such as cover 206 and reservoir 204 in FIG. 2A; loading and dispensing substances; loading and dispensing sealant to create a barrier, such as barrier 108 in FIG. 1A; mixing MicroChamber contents; washing a MicroChamber 602; and drying a MicroChamber 602, among others.

In some embodiments, the robotic device 640 includes a cover handling device 606 adapted to dispense covers of one or more sizes on reservoirs to form the MicroChambers 602. The cover handling device 606 can be adapted to retrieve loose covers from cover storage boxes 605 and/or other suitable location in or around the sample processing system 600. The robotic head 640 can further include a metering pump, a vacuum pump, cable train and printed circuit board containing components and devices for controlling the robotic head 640. The robotic head 640 can also incorporate a Lee Pump, a vacuum pump, optical sensors, coil latch solenoid, SMI horizontal slide, SMC vacuum switch, valves, and an Igus e-chain.

The cover storage box 605 can enable covers to be dispensed one at a time. The cover storage box 605 can be refillable and constructed from aluminum, stainless steel, plastic, or other suitable material. In some embodiments, the cover storage box 605 can be spring-loaded or otherwise configured to facilitate handling of the covers.

In further embodiments, movable covers can be formed with or attached to rack 642 adjacent one or more of the substrates. The covers can be positioned over and removed from the reservoirs with independently controlled actuators or by suitably configured robotic device(s) 640. The robotic device 640 or other suitable mechanism can be configured to wash and/or dry the movable covers before and/or after processing a sample. The covers may be replaced with the same or different type of cover, and may be embodied using any suitable form factor such as side-hinges, accordion shape, sliding, and/or dispensable tape.

The sample processing system 600 can be configured with one or more sensors to detect the position and orientation of the covers on the MicroChambers 602 or other locations in the sample processing system 600. In some embodiments, one or more of the sensors can be located on or in the movable arm 614 and/or robotic device 640. The sensors can also be located in a stationary position, in addition to, or instead of, being co-located with the movable arm 614 and/or robotic device 640.

In some embodiments, the sample processing system 600 can include a substance dispensing device 604 that is adapted to dispense one or more substances, such as a reagent, in the MicroChambers 602. The cover handling device 606 can operate in combination with the substance dispensing device 604 to automate placement and removal of the covers over the reservoirs at the appropriate time during the process.

A controller 608 can be included in the sample processing system 600 to execute logic instructions that control operations and functionality of components in the sample processing system 600, such as the substance dispensing device 604 and the cover handling device 606. The controller 608 can also be adapted to operate components in the sample processing system 600 to control the microenvironment in MicroChambers 602. Programmed logic instructions associated with particular protocols and processes can specify actions to be taken at particular times such as placing a cover on a MicroChamber 602, removing a cover from the MicroChamber 602, heating or cooling a reagent, dispensing a specified reagent to the MicroChamber 602; heating or cooling the MicroChamber 602, and/or washing the MicroChamber 602 and/or cover, among others. For example, a particular process can be associated with a particular MicroChamber 602 or group of MicroChambers 602 via a user interface. The process can specify dispensing a first reagent to a reservoir containing a sample, placing and sealing a cover on the reservoir to form a MicroChamber 602, removing the cover from the MicroChamber 602, washing the reagent from the MicroChamber 602, drying the MicroChamber 602, dispensing a second selected reagent to the MicroChamber 602, again covering the MicroChamber 602, and selectively repeating the various actions.

Figure 7:
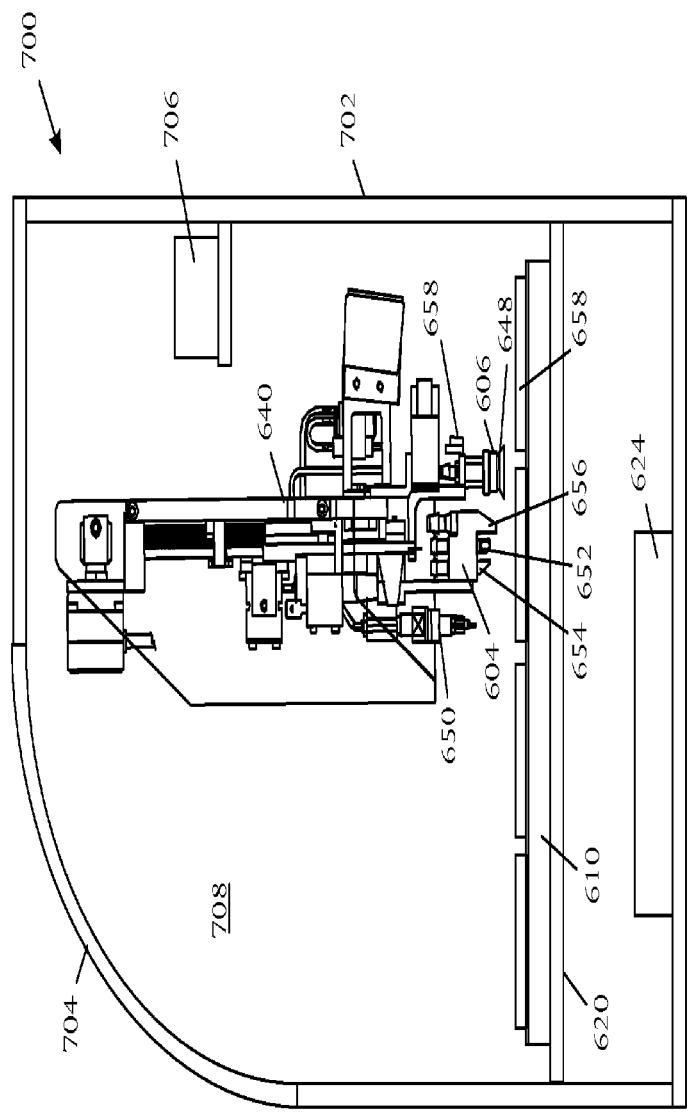
FIG. 7 shows an embodiment of a sample processing system including a humidity controller.

Referring to FIG. 7, an embodiment of a sample processing system 700 including a humidity controller 706 is shown to control humidity in the internal cabinet environment enclosed by framework 702 and cabinet 704. The humidity controller 706 can operate independently; or be controlled by the controller 608 or other suitable control device in combination with operation of other components in the sample processing system 600. Typically, humidity in the sample processing system 600 can be adjusted to a level that helps prevent evaporation of contents in the MicroChambers 602. However, in some instances humidity can be controlled for a specimen(s) in a particular MicroChamber or group of Micro Chambers 602. For example, the controller 608 can adjust humidity within the system MicroChamber 708 prior to and during exposure of the contents of one or more of the MicroChambers 602 when a cover is not in place.

Referring to FIGS. 8A-8D, embodiments of various devices that can be used as the cover handling device 606 of FIGS. 6A-6C are shown. An effector 806 is coupled to a robotic head 804. One or more dispensers 802 can dispense covers of one or more different sizes or other characteristics. The robotic head 804 is adapted to move to the vicinity of the dispenser 802 to allow the effector 806 to retrieve a cover from the dispenser 802. The effector 806 can be operated to perform multiple functions including placing and removing covers from a substrate, such as substrate 202 in FIG. 2A.

Figure 8A:
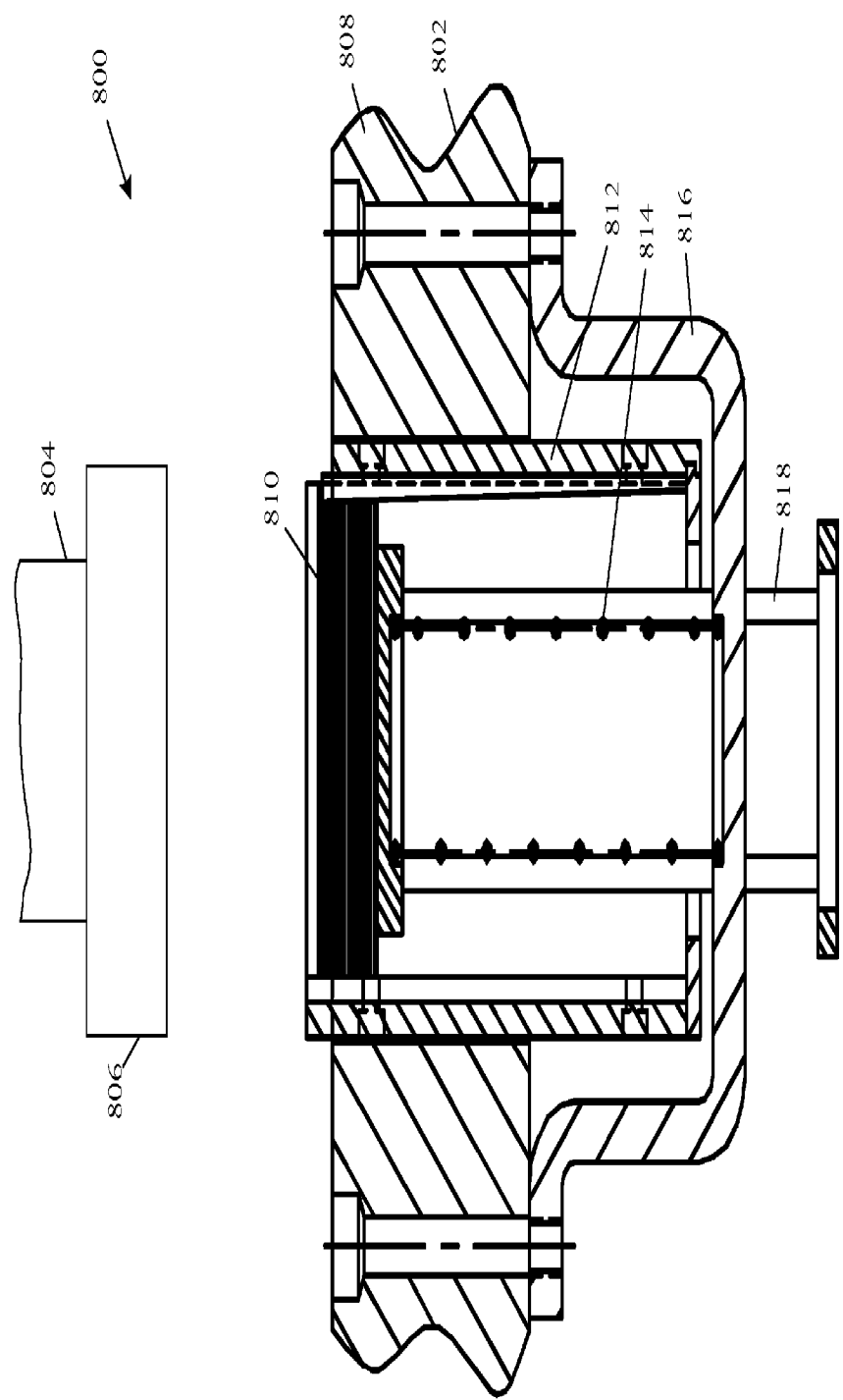
FIGS. 8A-8F show embodiments of various devices that can be used as the cover handling device of FIGS. 6A-6E.
Figure 8B:
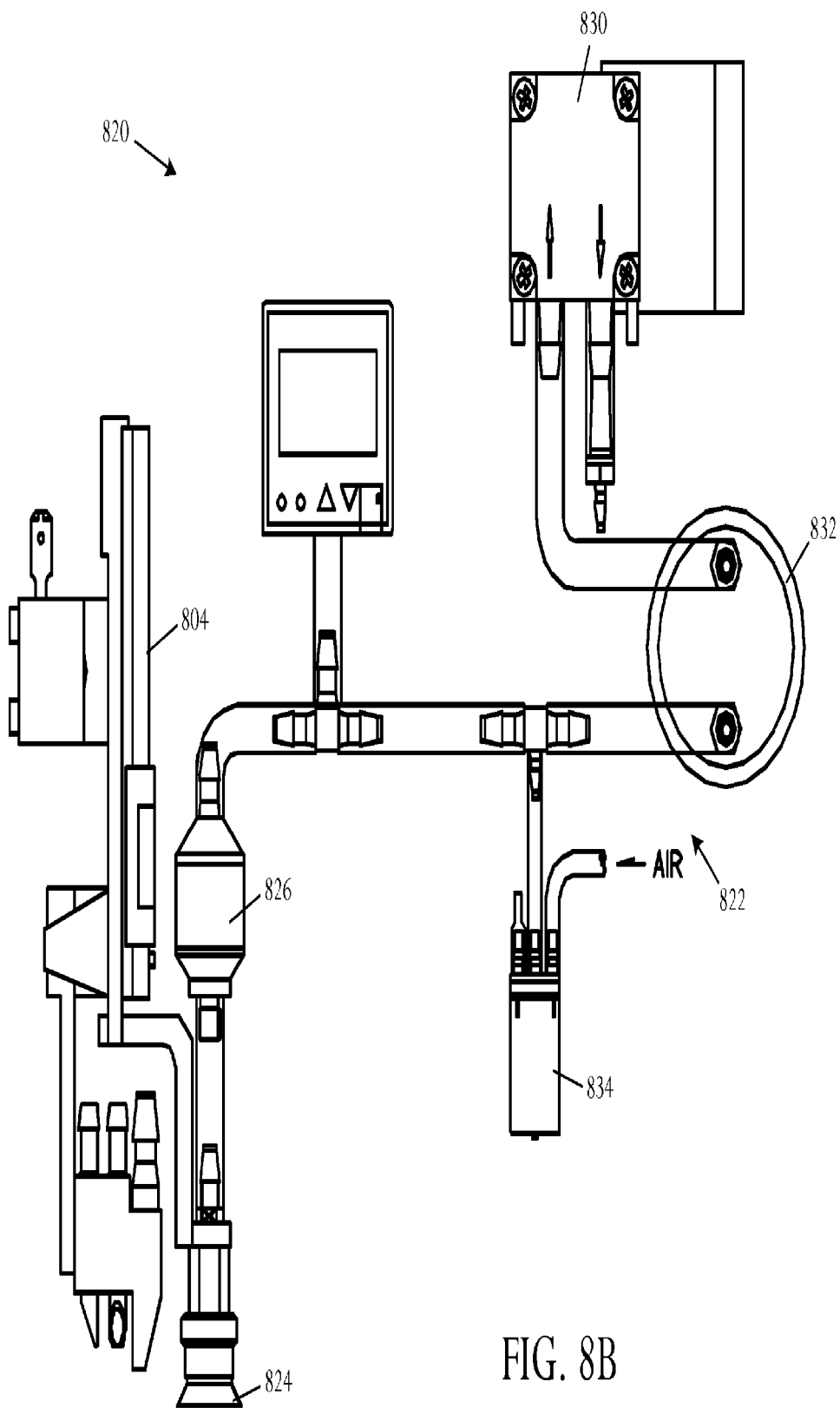

FIG. 8B shows an embodiment of cover handling system 820 that includes a vacuum system 822 including a vacuum pad effector 824 that grips and releases the covers. The vacuum system 822 can include a water separator 826, a vacuum sensor 828, a vacuum pump 830, a vacuum buffer 832, and/or an air valve 834. The vacuum sensor 828 can be configured to supply signals to controller 608 (FIG. 6A) to control operation of the cover handling system 820.

When vacuum sensor 828 indicates increased pressure, logic in controller 608 assumes that a cover is obstructing an opening in effector 824 through which vacuum pressure is exerted by the vacuum pump 830. After a cover is placed in position, the vacuum pump 830 is turned off and the air valve 834 opens, enabling positive air pressure to push the cover off the vacuum pad effector 824. The operation prevents the cover from adhering to the vacuum pad effector 824.

Figure 8C:
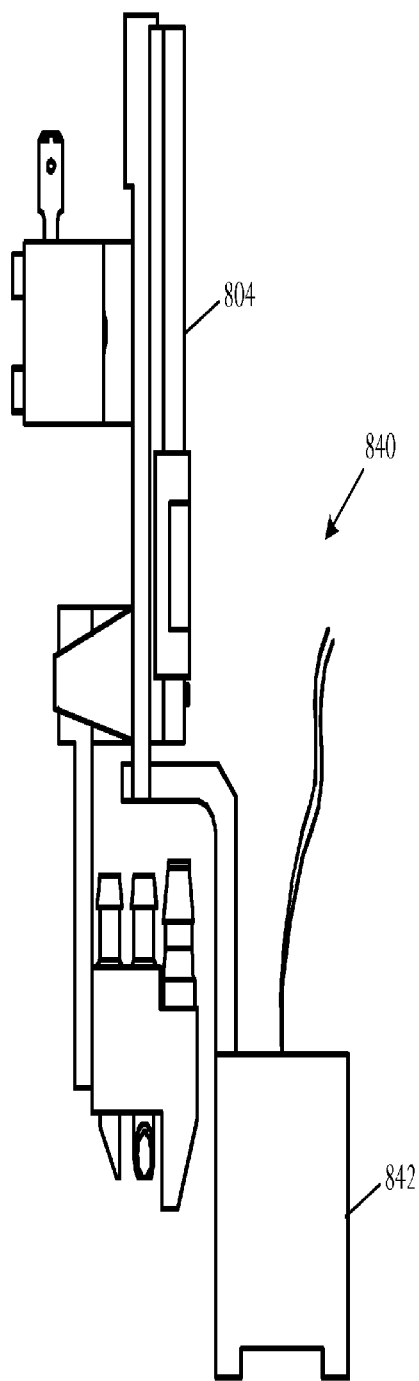

FIG. 8C shows an embodiment with an electromagnetic effector 840 further comprising an electromagnetic attachment device 842 that grips and releases the covers. In such embodiments, covers are configured with one or more magnetic portions. For example, the cover may be configured with a magnetic paint or coating, chemical coating, a conductive material, foil, or other suitable material. The material can be embossed or otherwise configured to prevent covers from adhering. The electromagnetic attachment device 842 can be operated to generate positive and negative electrical fields that attract and repel the magnetic material on the covers.

Figure 8D:
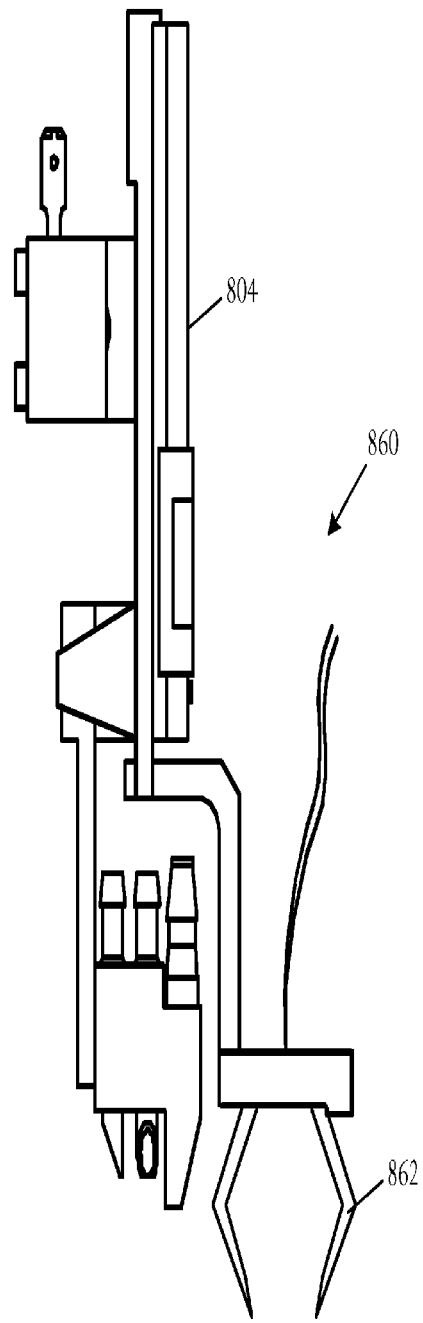
Figures 8E, 8F:
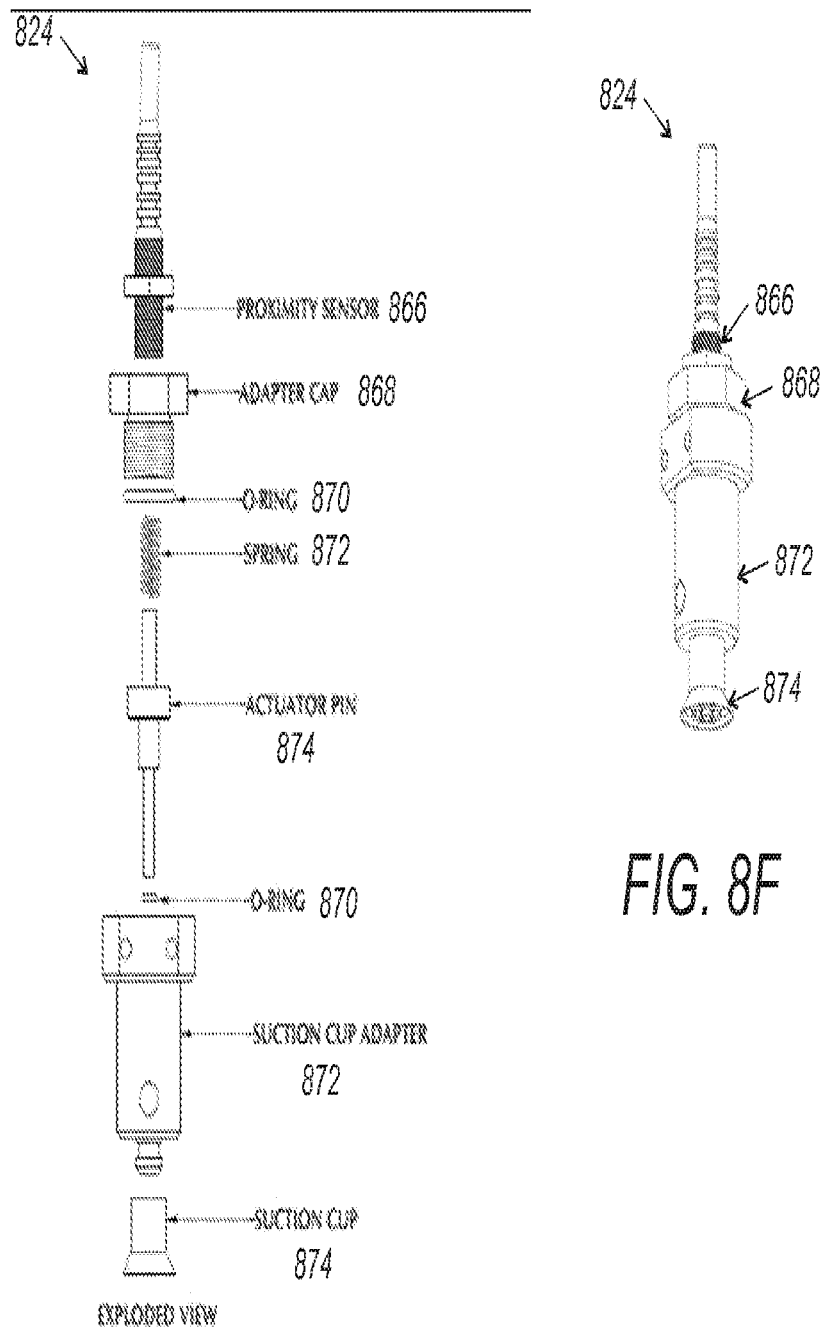

FIG. 8D illustrates an embodiment with an effector 860 further comprising a mechanical gripper device 862 that grips and releases the covers. The gripper device 862 can be padded, coated with rubber, or other suitable substance to facilitate handling of the covers.

In the various embodiments, the controller 608 controls operation of the robotic head 804 and the effectors 806, 824, 842, 862. A program code executed by the controller 608 is adapted to control removal of a cover from the substrate without disturbing the sample or substrate. In some embodiments, the effector 806, 824, 842, 862 and the robotic head 804 may be configured to move independently of one another. Note that other suitable devices can be utilized, in addition to, or instead of effectors 806, 824, 842, 862.

Referring to FIGS. 6A and 6B, in some embodiments, a pipette tip 626 can be used as the oil pen and grasped by the pipette tip adapter 652. The pipette tip 626 can be dipped in a reservoir of sealing substance, such as oil, to pick up a precise amount of sealing substance. The sealing substance can be dispensed in any programmed pattern by moving the robotic device 640. The pipette tip 626 can be discarded after usage.

Figure 9A:
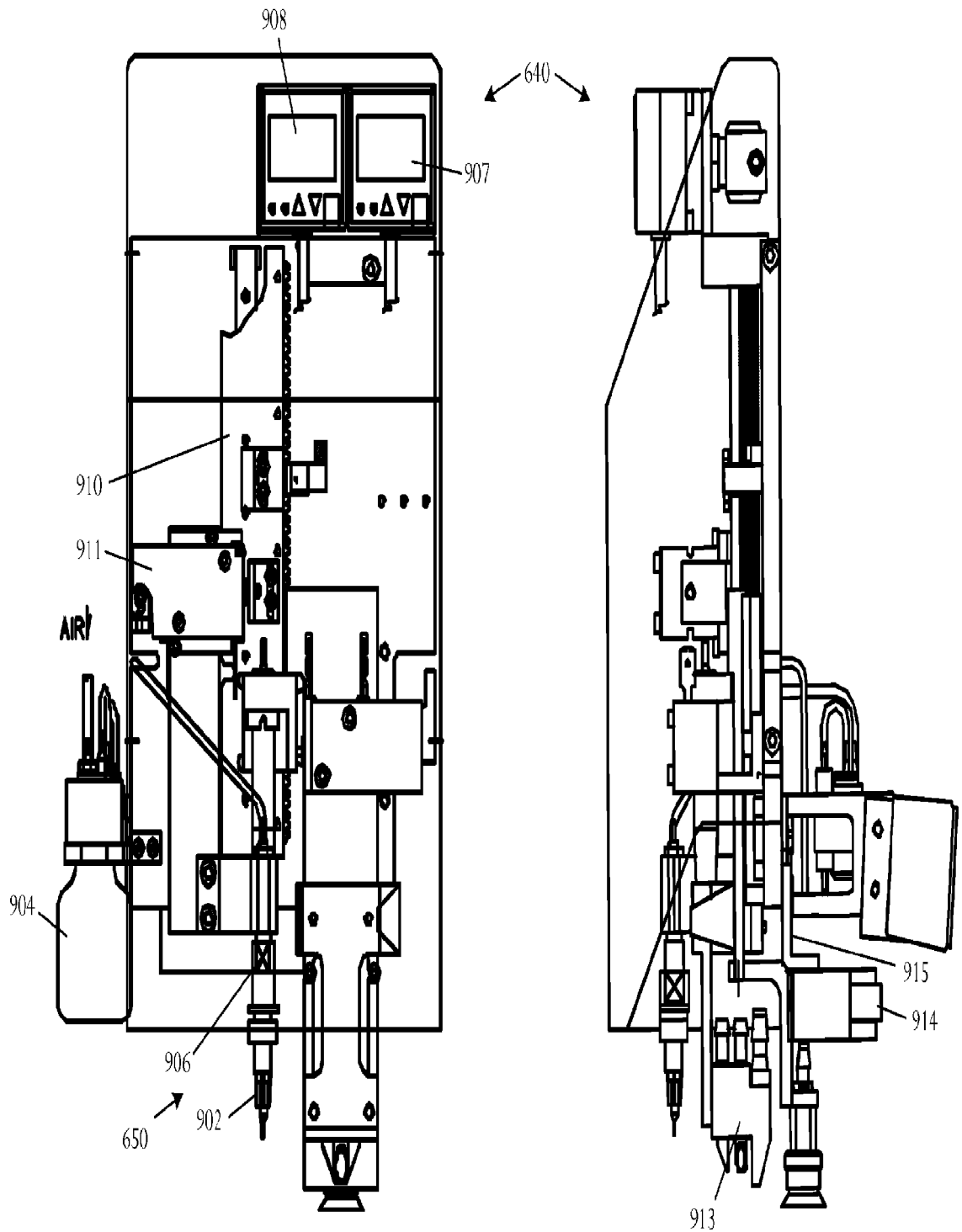
FIG. 9A shows an embodiment of a sealing assembly as an attachment to the robotic device of FIGS. 6A-6E.
Figure 9B:
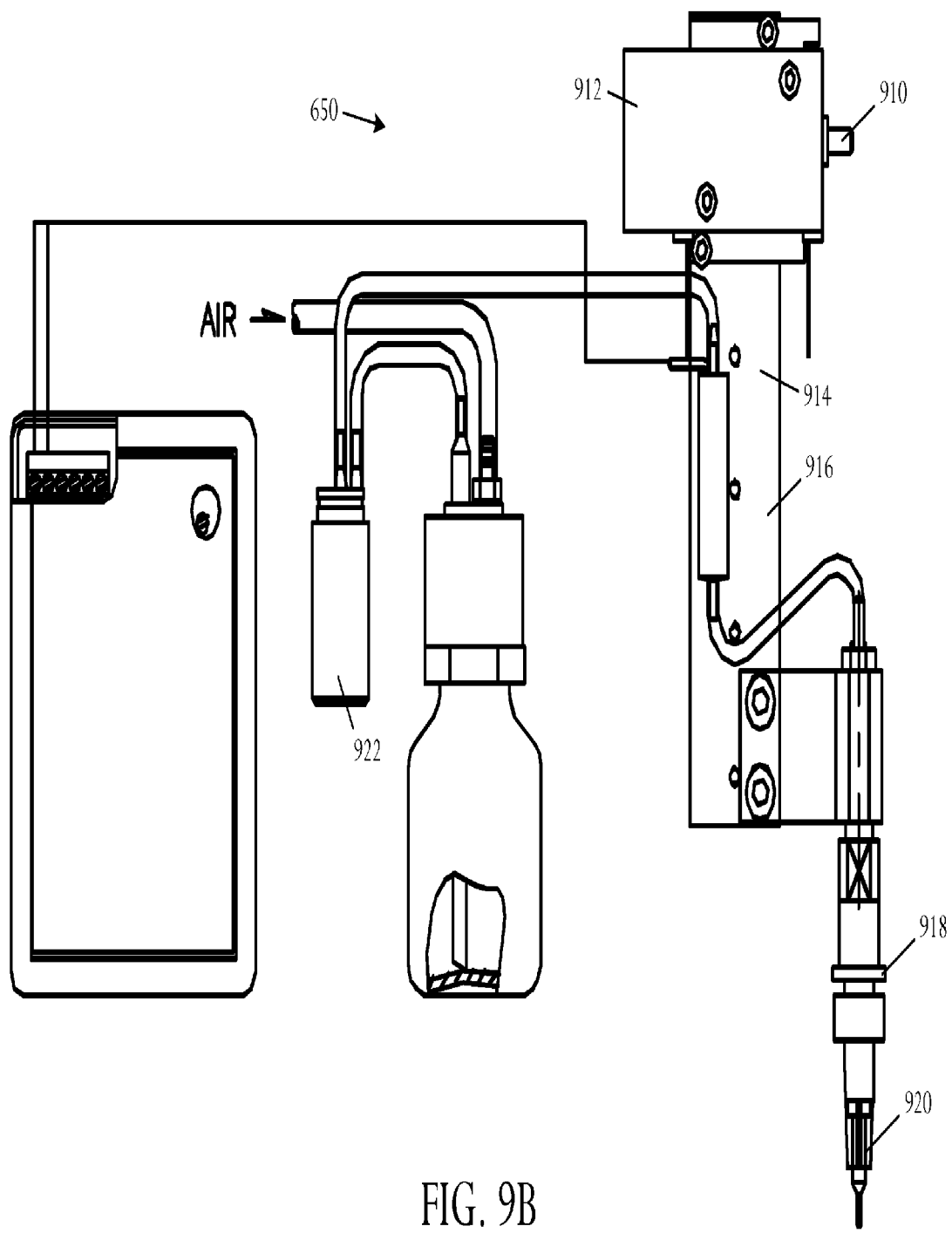
FIG. 9B shows an embodiment of the sealant assembly configured independently of the robotic device of FIGS. 6A-6E.

In other embodiments, the sample processing system 600 may include a sealing assembly 650. Referring to FIGS. 9A and 9B, FIG. 9A illustrates the sealing assembly 650 as an attachment to the robotic device 640. FIG. 9B shows an embodiment of the sealant assembly 650 configured independently of the robotic device 640. Sealing assembly 650 can include a sealant pen 902, a sealant reservoir 904 coupled to the sealant pen 902, a sealant valve controller 908, and a sealant pen valve 906 that can be operated to selectively eject a pattern of sealant to form a barrier such as barrier 108 (FIG. 1A) around a reservoir 104, and/or to seal a cover over the reservoir. The sealant pen 902 can include an application attachment such as a syringe or needle. The sealant reservoir 904 contains a suitable sealing material such as a sealing oil, wax, polymer, or suitable substances. The sealant valve controller 908 enables the valve 906 to operate at a controlled frequency to facilitate precise sealant flow control.

The sealant valve controller 908 allows control of the rate and/or volume of sealant flow. The sealant pen 902 can be constructed from polypropylene, stainless steel, Teflon™, Delrin™, or other suitable material. The sealant can create a permanent seal or a non-permanent seal, depending on the particular sealant applied. In a particular example, a sealant material such as particular polymers can be used to form a seal above a specified temperature and break the seal below specified temperatures, or vice versa.

The controller 608 can also control the sealing assembly 650 to seal a MicroChamber 602 while reducing or eliminating trapped air bubbles. For example, the sealant can be positioned in a configuration that enables bubbles to flow from the MicroChamber such as by leaving an opening in the sealant to allow trapped bubbles to escape.

Figure 10A:
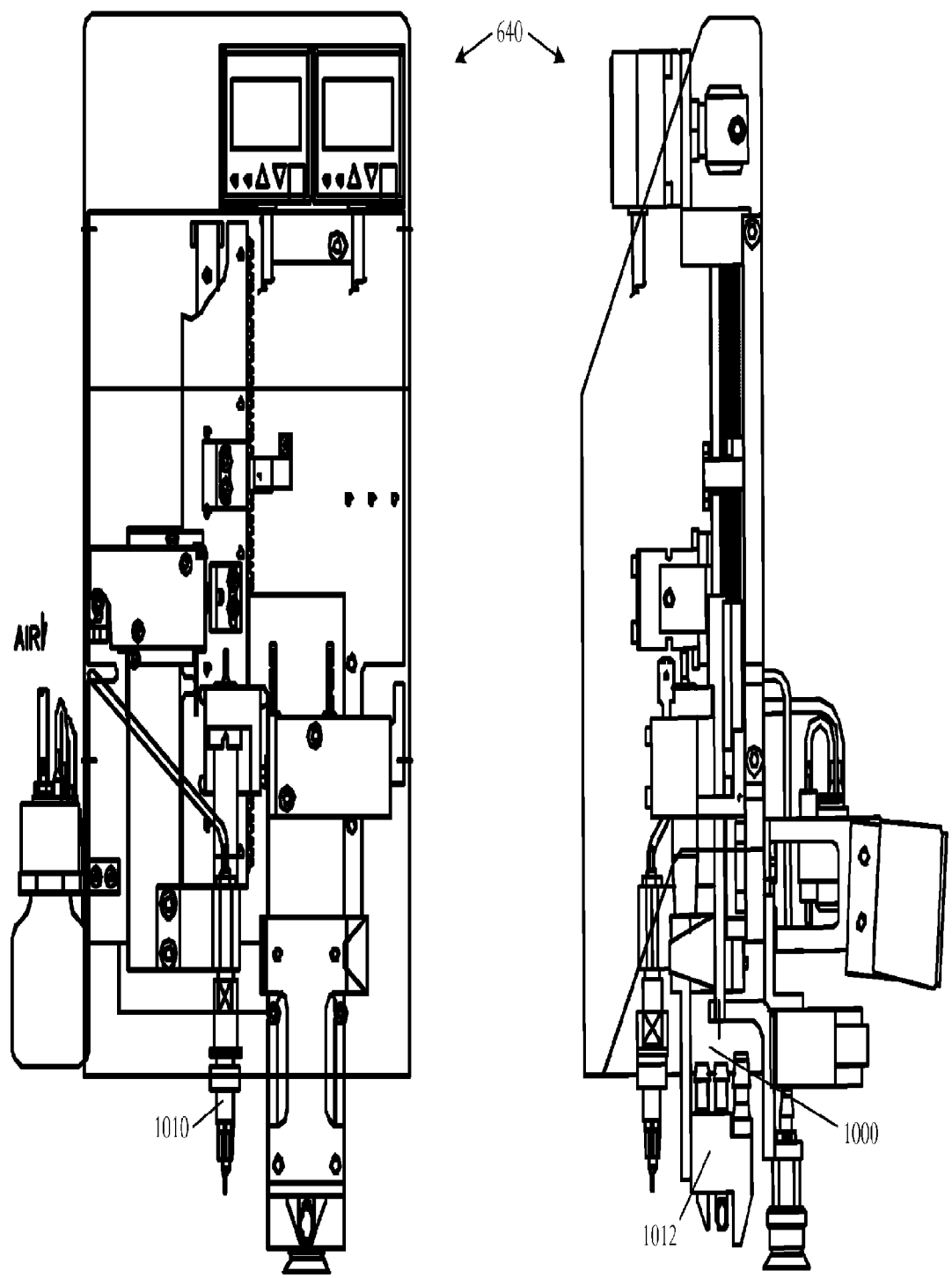
FIGS. 10A-10K show an embodiment of reagent dispensing device of the robotic device of FIGS. 6A-6E.
Figure 10B:
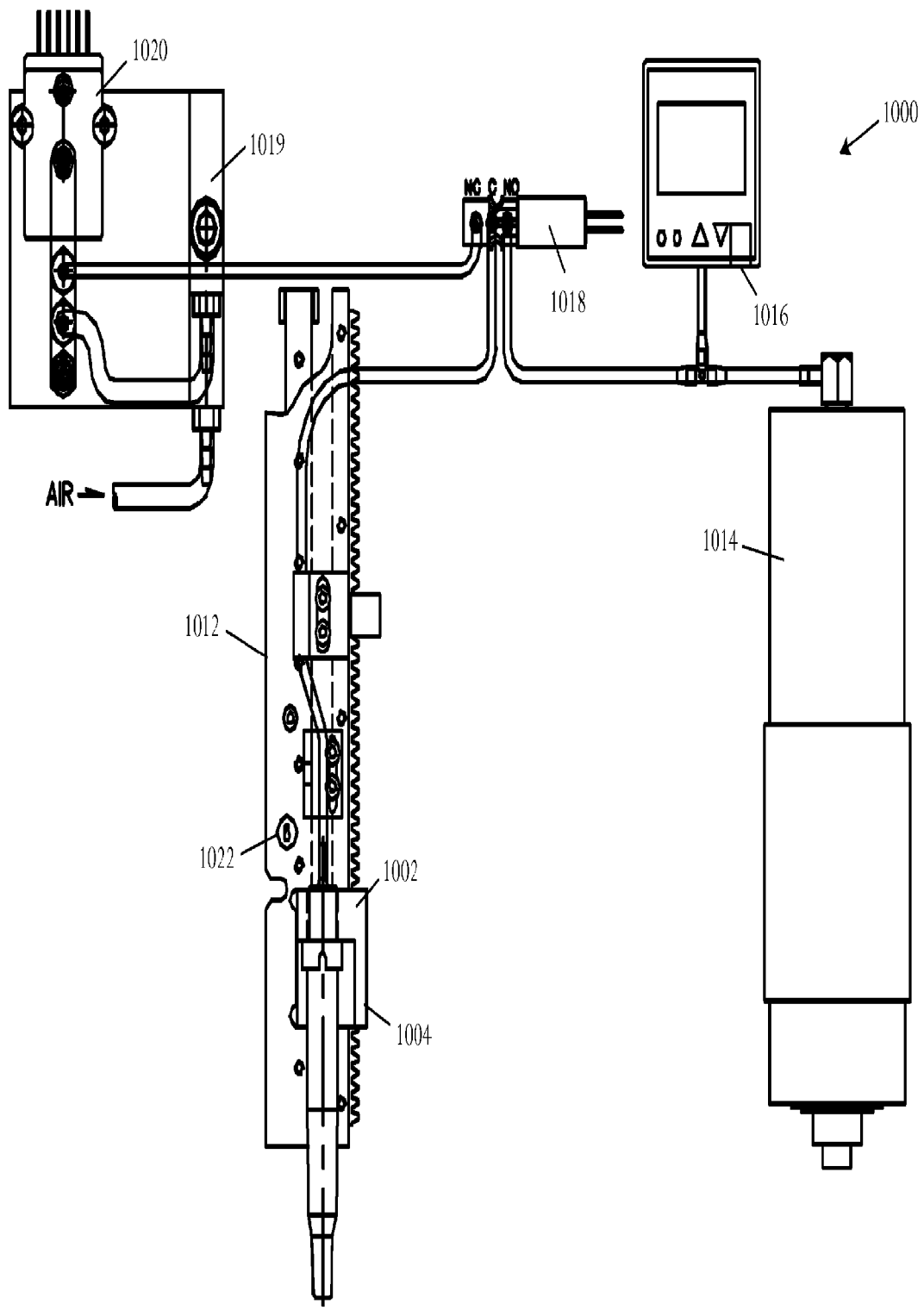
Figures 10C, 10D:
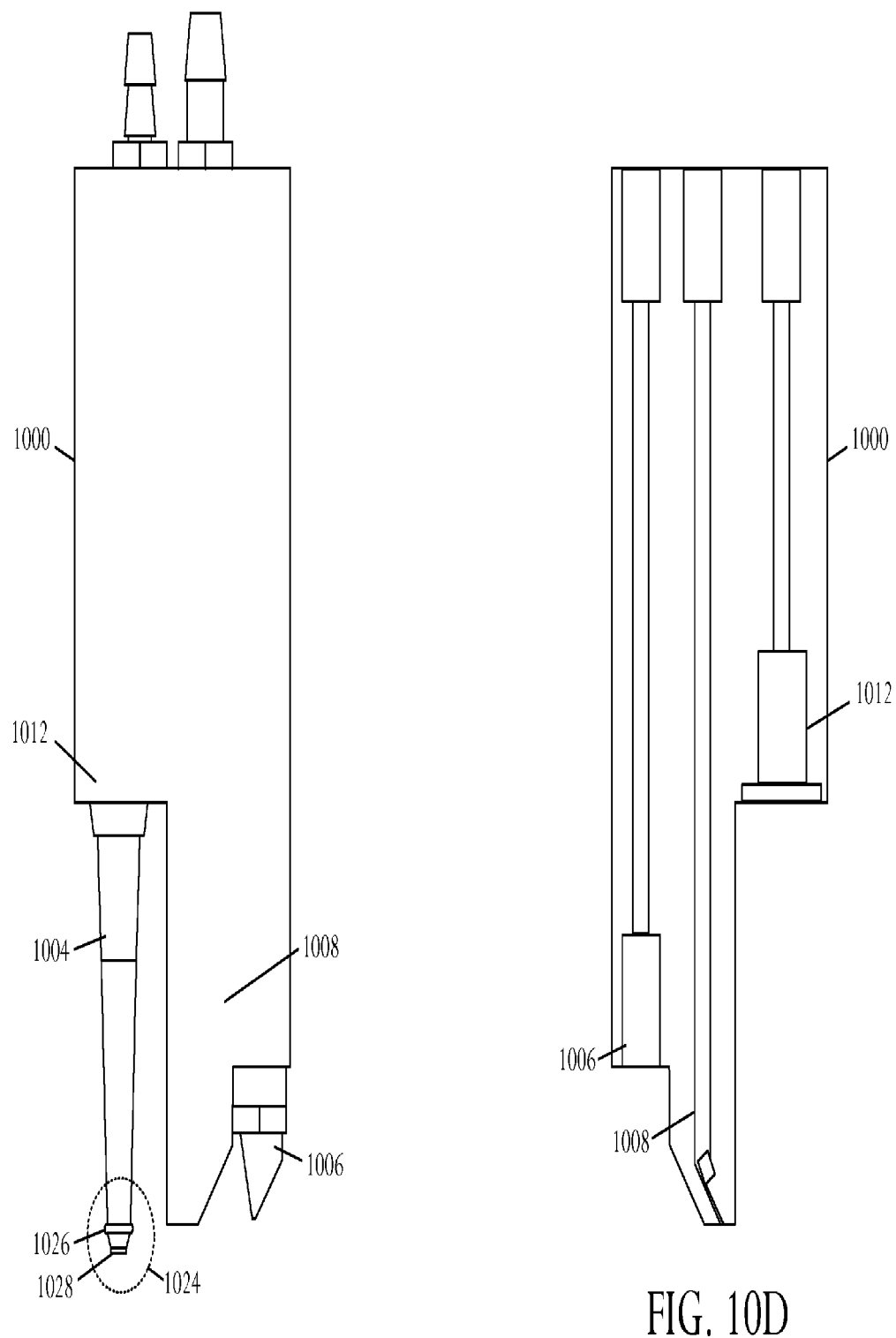
Figure 10E:
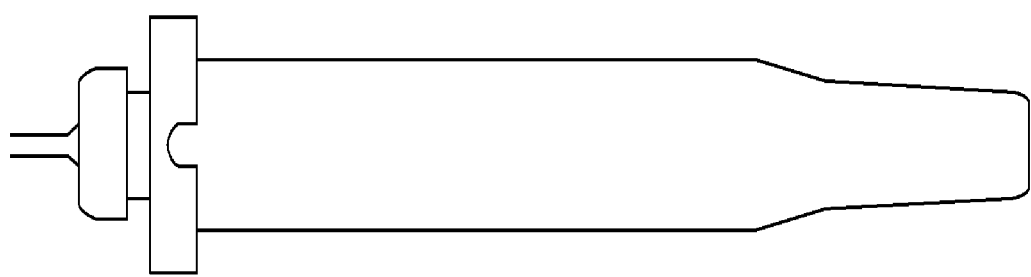
Figure 10F:
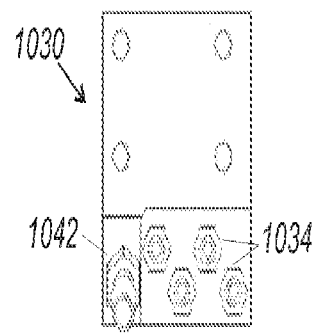
Figure 10K:
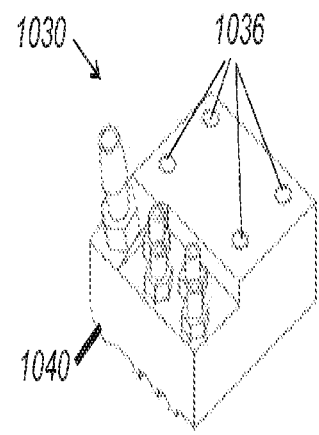
Figure 10G:
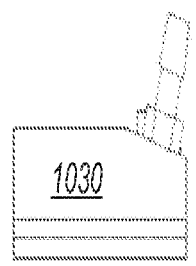
Figure 10H:
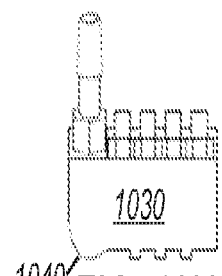
Figure 10I:
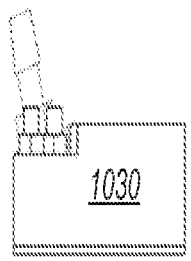
Figure 10J:
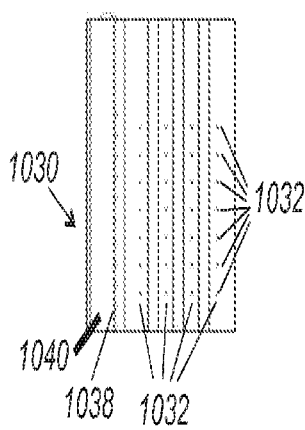

The sample processing system can aspirate a micro-volume of a selected probe and dispense the micro-volume on a sample enclosed by a barrier, such as a hydrophobic barrier, on the substrate, or on a sample on a non-barrier substrate. Referring to FIGS. 10A-10E, schematic pictorial diagrams illustrate an embodiment of a reagent dispensing device 1000 adapted for usage in the illustrative sample processing systems. FIG. 10A shows an embodiment of the dispenser 1000 attached to the robotic device 640. FIG. 10B is a more detailed view showing the dispenser 1000 alone. FIG. 10C is a side view of the reagent tip head in attachment with the robotic device 640. FIG. 10D shows a cross-sectional view of the reagent tip head. FIG. 10E is a cross-sectional view showing a pipette tip adapter. The reagent dispensing device 1000 comprises a liquid dispenser 1002 that dispenses liquid to a chemical and/or biological sample on a substrate in a selected volume range including a capability to consistently dispense a selected liquid in volumes as low as 0.1 ul. The reagent dispensing device 1000 further comprises a pipette tip handling device 1004 coupled to the liquid dispenser 1002 that aspirates and dispenses a micro-volume of the selected liquid via a pipette tip selected from among multiple different sized pipette tips.

In a particular embodiment, the pipette tip handling device 1004 is configured to handle a plurality of pipette tip sizes including a first size with a size range from hundreds to thousands of microliters and a second size with a size range of tenths to hundreds of microliters.

The reagent dispensing device 1000 can further comprise a wash head 1006 and a blow head 1008. The wash head 1006 is coupled to the pipette tip handling device 1004 and configured to deliver multiple selected bulk solutions in various controlled volumes to a sample substrate. In a particular embodiment, the wash head 1006 delivers a bulk solution in a range from tens to hundreds of microliters (μl). The blow head 1008 is coupled to the pipette tip handling device 1004 and configured to programmably blow air or any gas over the sample, for example to remove excess liquid from the sample.

The illustrative pipette tip handling device 1024, attached to a robotic device 640 in the form of a Z-head that executes motion in a Z-direction, can be use two different sizes of pipette tips interchangeably by virtue of usage of a tip adapter having a two-taper design. The design enables the tip adapter 1026 to pick up more than one pipette tip size, enabling precision dispensing in a range from 0.1 ul to 1000 ul or more. The tip adapter 1026 can have multiple tapers to fit different size tip barrels. A photoelectric tip sensor 1028 is used to determine contact with a tip.

An illustrative wash head 1006 is capable of delivering six different bulk solutions in any volume selected by a process. The blow head 1008 dries a substrate in preparation for the next step in a process. The aspiration system can consistently aspirate and dispense any volume in a range from 0.5 microliters (μl) to one milliliter (ml). In some embodiments, pipette tips can be detected using a laser sensor.

A sealant pen 1010 is configured to programmably dispense a selected amount of sealant in a programmed pattern on the sample substrate. The sealant is applied to seal a microchamber cover.

A reagent head 1012 is coupled to the pipette tip handling device 1004 and adapted to deliver a reagent volume to the sample substrate in a range from sub-microliters (μl) to milliliters (ml).

In some embodiments, the reagent dispensing device 1000 can be attached to a robotic head, such as a Proportional Integral Differential (PID), Proporational-Integrative (PI), or other scheme motion controller head, that can move relative to the sample substrate. The sealant pen 1010 can be coupled to the pipette tip handling device 1004 and adapted to programmably dispense a selected amount of sealant in a programmed pattern on the sample substrate. The sealant can be applied to seal a micro-chamber cover.

For example, the reagent dispensing device 1000 can be used in a sample processing system that includes a stationary platform configured to hold a plurality of substrates. The moveable robotic head can be coupled to the liquid dispenser 1002 and the pipette tip handling device 1004. The robotic head moves relative to the substrates and is programmable to automatically process the substrates and uniformly aspirate and dispense a selected liquid micro-volume. In another embodiment, the substrate holding platform may be moving platform and the moving robotic head moves relative to the moving substrates.

In a typical application, a controller in the sample processing system can be programmed or controlled to control the liquid dispenser 1002 and the pipette tip handling device 1004. The controller controls aspiration of a micro-volume of a fluid or reagent probe and dispensing of the micro-volume in a region constrained by a barrier containing a sample on a substrate. Similarly, the controller can control aspiration of a micro-volume of a probe and dispensing of the micro-volume on a sample on a non-barrier substrate.

Referring to FIGS. 6A-6C, the temperature control assembly 610 with active heating and cooling components can also be included in some embodiments of the sample processing system 600. The controller 608, or other suitable device, can be coupled to operate the temperature control assembly 610 to control the temperature environment in MicroChambers 602 by selective heating and cooling during specified phases of a protocol. The temperature of the MicroChambers 602 can be controlled individually or collectively, as specified by the process or protocol selected for the particular MicroChamber 602 or group of MicroChambers 602.

The temperature control assembly 610 can include active heating and cooling components for multiple slides or any relatively flat substrate, for example flat thermally-conductive substrates, such as glass slides, array silicon or glass chips, polymer/plastic substrates, and the like. Individual heating and cooling positions can be independently controlled. FIGS. 11A-11G depict various embodiments of temperature control assemblies 610 comprising multiple temperature control elements 1100. The platform 630 has capacity to hold multiple substrates in contact with multiple temperature control elements 1100. The platform 630 can be removed from the sample processing system and can be used for slide storage. The platform 630 can be constructed from materials that reduce or minimize thermal convection and hold a substrate secure during removal of a MicroChamber 602 from a substrate.

The temperature control assembly 610 can enable rapid temperature response and high controllability of the individual heating and cooling positions. Rapid temperature control enables processing phases with very short duration temperature steps. The illustrative combination of heating and cooling elements, base, and heat exchangers enables a high range of dynamic temperature control, for example form −4° C. to +110° C. and negligible cross-talk between adjacent positions. The illustrative temperature control assembly 610 also enables performance of multiple diverse applications simultaneously.

The temperature control assembly 610 can have a relatively thin base plate on which heating elements are mounted. The base plate functions as an efficient heat sink with fins attached on a planar surface. A particular temperature control implementation may include individual slide temperature control and cycling by active active heating and cooling with solid state sensor feedback, rapid heating and cooling cycles both less than two minutes, an operating temperature of ambient to 110° C., cross-talk between elements of less than 2° C., and uniformity across the heater top from edge to center of 18° C. For example, an illustrative system that uses thermal electric heater/coolers (TEC) with active cooling can attain a temperature range of −4° C. to 110° C. In other embodiments, any suitable temperature specifications may be implemented.

Figure 11A:
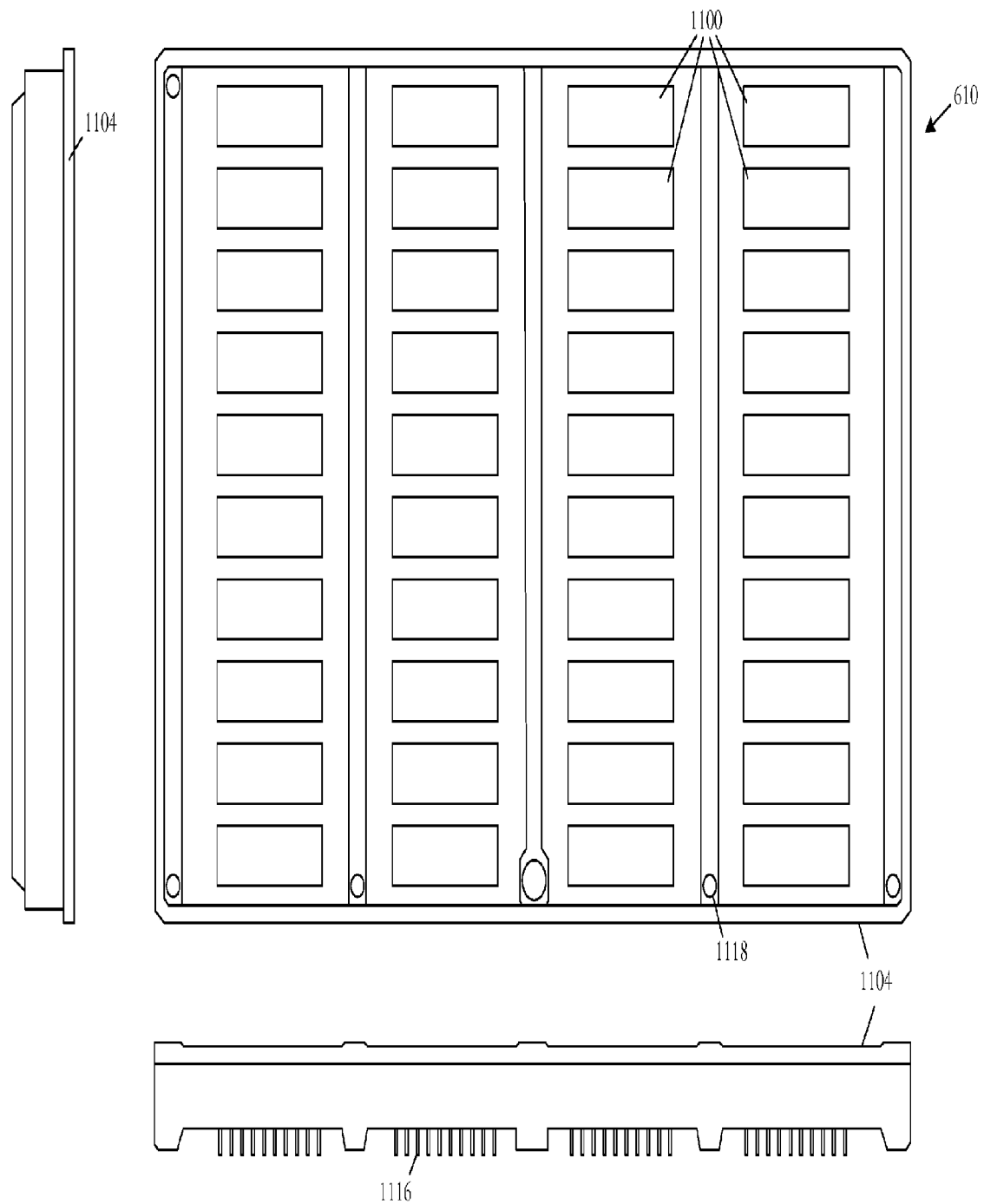
FIGS. 11A-11H are pictorial views showing various embodiments of temperature control assemblies that enable independent heating and cooling of multiple temperature control elements.

FIG. 11A depicts top and cross-sectional views of the temperature control base assembly 1104. The temperature control base 1104 has one or more individually controlled temperature modules. Heater assemblies are configured to heat or cool substrates such as glass slides or a flat substrate, such as a thermally-conductive substrate. In the illustrative embodiment, the temperature control base 1104 has integrated heating fins that function as heat exchangers.

Figure 11B:
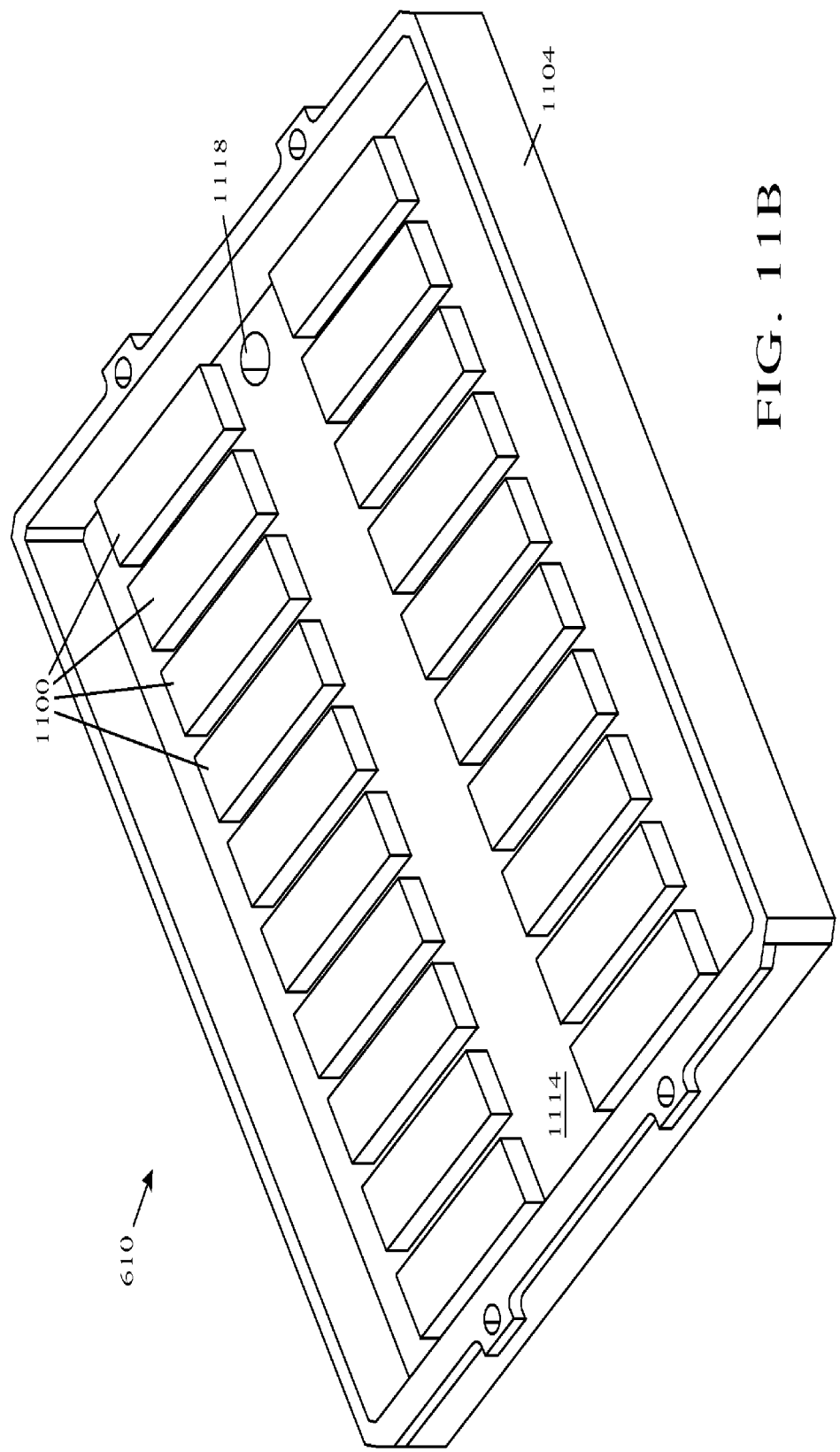

FIG. 11B illustrates a perspective view of the temperature control base 1104 and an included array of temperature control elements 1100. The temperature control base 1104 may be constructed from aluminum or other suitable material and fabricated with cooling fins that can be integrated into a fabricated part. The temperature control base 1104 can also enable fluid containment and drainage. Multiple heater assemblies can be assembled to the temperature control base 1104.

The temperature control assembly 610 can include multiple temperature control elements 1100. The individual temperature control elements 1100 comprise a thermally-conductive temperature application top 1102 configured to make contact to a corresponding substrate. Examples of suitable temperature control elements 1100 include resistance heaters and heat/cool Thermo-Electric Coolers (TEC).

The temperature control assembly 610 further comprises a temperature control base 1104 coupled to a plurality of individual temperature control elements 1100. The temperature control base 1104 is typically constructed from temperature and chemical resistant polymers or metals such as polypropylene, Kynar™, Teflon™, fluoropolymers, aluminum, and stainless steel. The temperature control base 1104 can also function as a waste drain tray for process fluids.

A thermal-conducting metal plate 1106, a temperature-sensing device 1108, a resistive heater or thermal electric heater 1110, and a sealed housing 1112 that thermally, chemically, and electrically isolates the individual substrate temperature control elements 1100 can be included in the temperature control assembly 610.

The temperature control assembly 610 may further comprise a waste drain tray 1114 attached to the temperature control base 1104. Waste liquid can be handled by gravity flow or a diverter valve and pump system to isolate hazardous and non-hazardous waste flows.

Referring again to FIGS. 6A-6C, the controller 608 can control the temperature applied to individual substrate positions of the platform 630 according to sensor feedback from the temperature control assembly 610. Various temperature control operations that can be executed by the controller 608 include, for example, executing temperature-controlled hybridization and staining simultaneously on different substrates, controlling automatic processing of DNA and protein microchips, controlling automatic processing of tissue arrays, Fluorescence In Situ Hybridization (FISH), In Situ Hybridization (ISH), and Immunohistochemistry (IHC) samples, and automatically controlling user-determined substrate temperature and incubation times. The controller can perform a combination of the various processes on a sample. Other possible operations include automatically controlling over-temperature protection and safety control, controlling active heating and cooling of the individual substrates to a selected temperature set-point, and controlling automatic active heating and cooling of a MicroChamber to a high temperature and holding the temperature for a selected time without loss of a significant quantity of fluid.

The multiple individually controllable temperature control elements 1100 can be coupled to the temperature control base 1104, for example by integrally forming the temperature control modules 1100 into the temperature control base 1104 or installing the temperature control modules 1100 using a coupling, for example screws, bolts, clips, clasps, or other attachment or mounting devices.

The illustrative temperature control modules 1100, for example also called temperature control elements or temperature application elements, are generally constructed from a thermally-conductive material and may be adapted for removable positioning adjacent the temperature control base 1104.

In some embodiments, the temperature application elements 1100 can be configured for pluggable or insertable entry to a socket or connectors located on the temperature control base 1104. In such embodiments, the temperature application element 1100 further includes a plug or connectors that connect to corresponding connectors or a socket on the temperature control base 1104.

Optionally, in some embodiments the individual temperature control modules 1100, for a single position in the temperature control base 1104, may further comprise one or more vibrators 1126 that induce mixing in the MicroChambers on the substrates. In various embodiments, the vibrators 1126 may be embedded into the temperature control elements 1100, attached to the temperature control elements 1100, or positioned remote from the temperature control elements 1100. The vibrators may be mechanical oscillators, electric oscillators, piezo-electric elements, ultrasonic pulse devices, devices that produce oscillation based on application of heat, and/or other suitable devices.

Figure 11C:
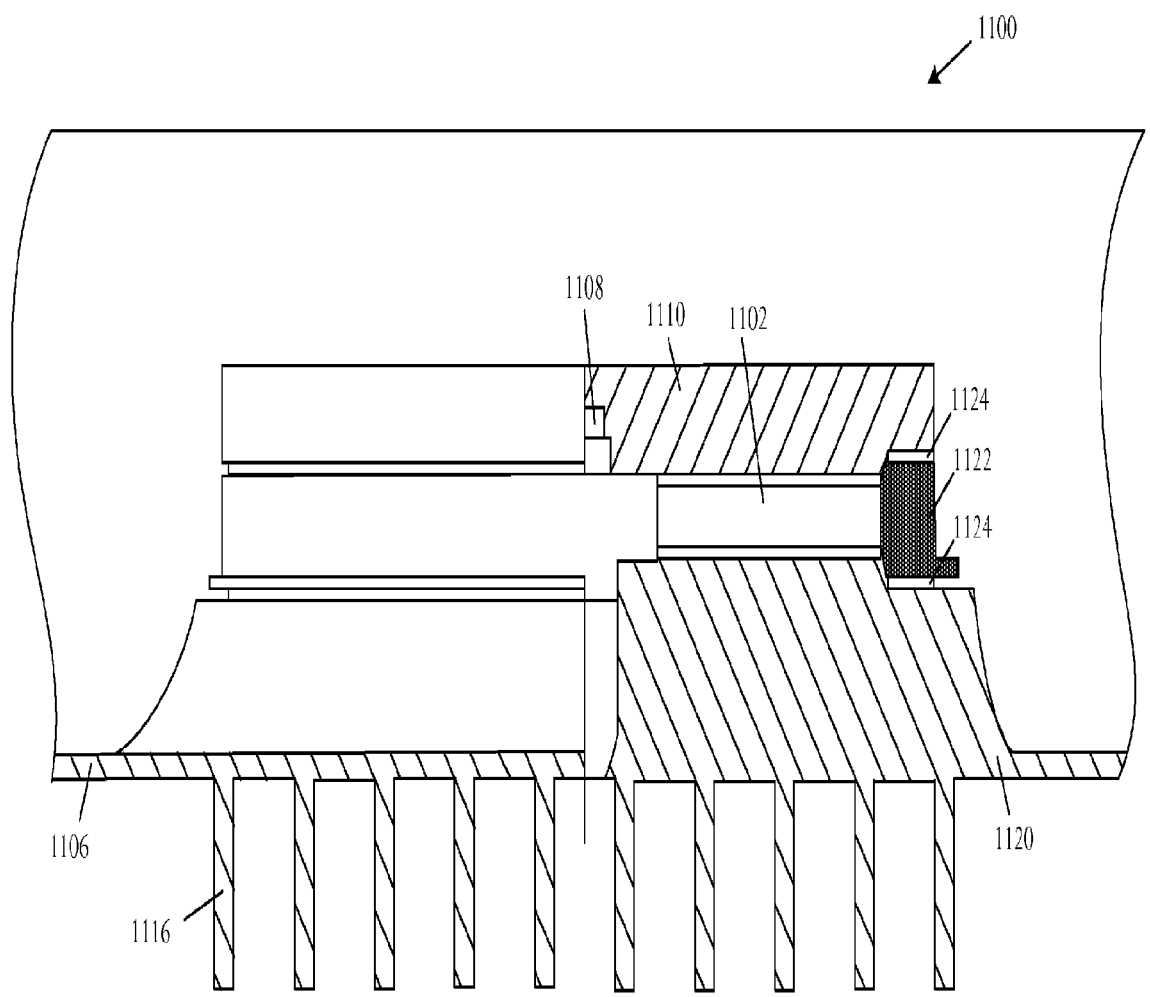
Figure 11D:
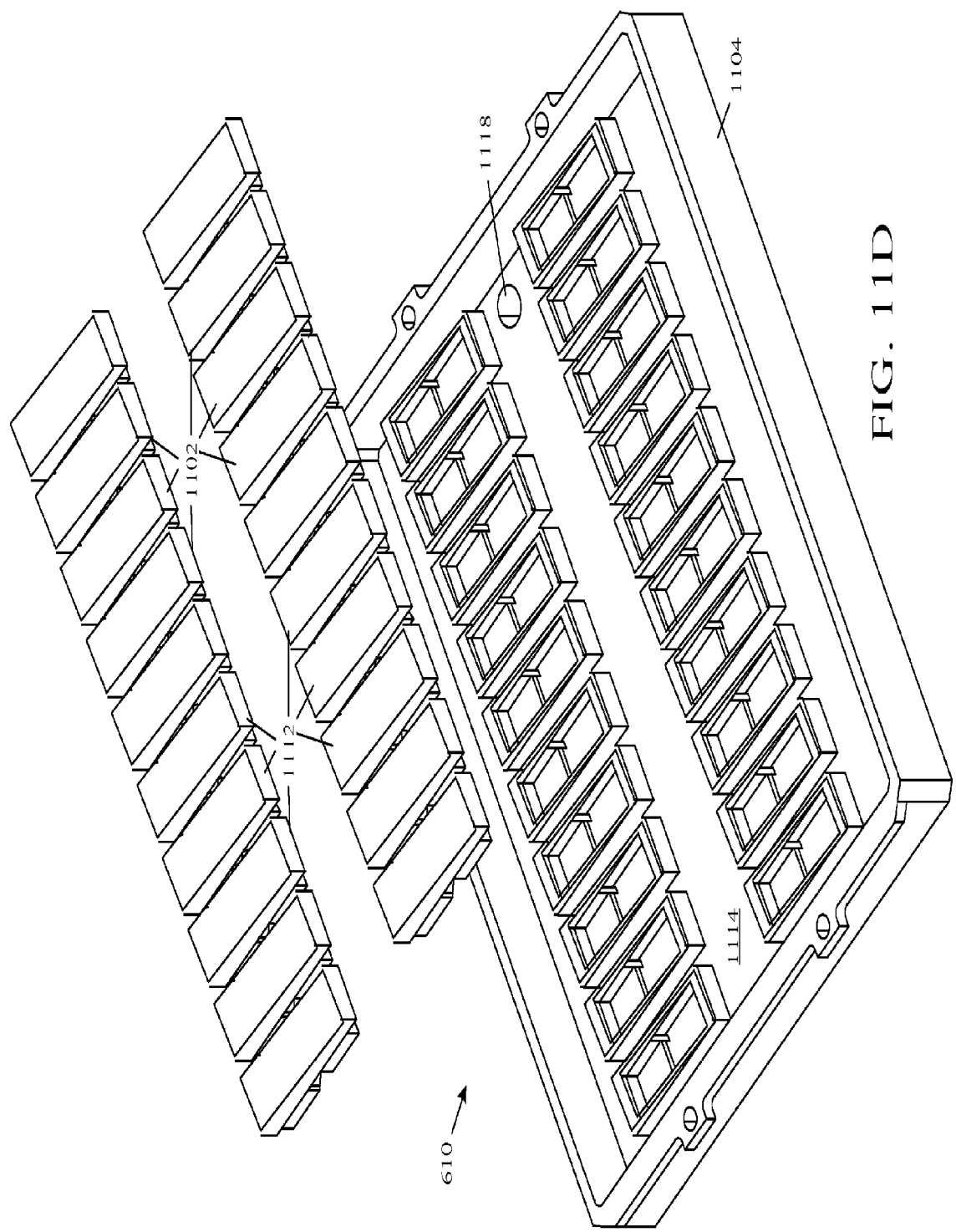
Figure 11E:
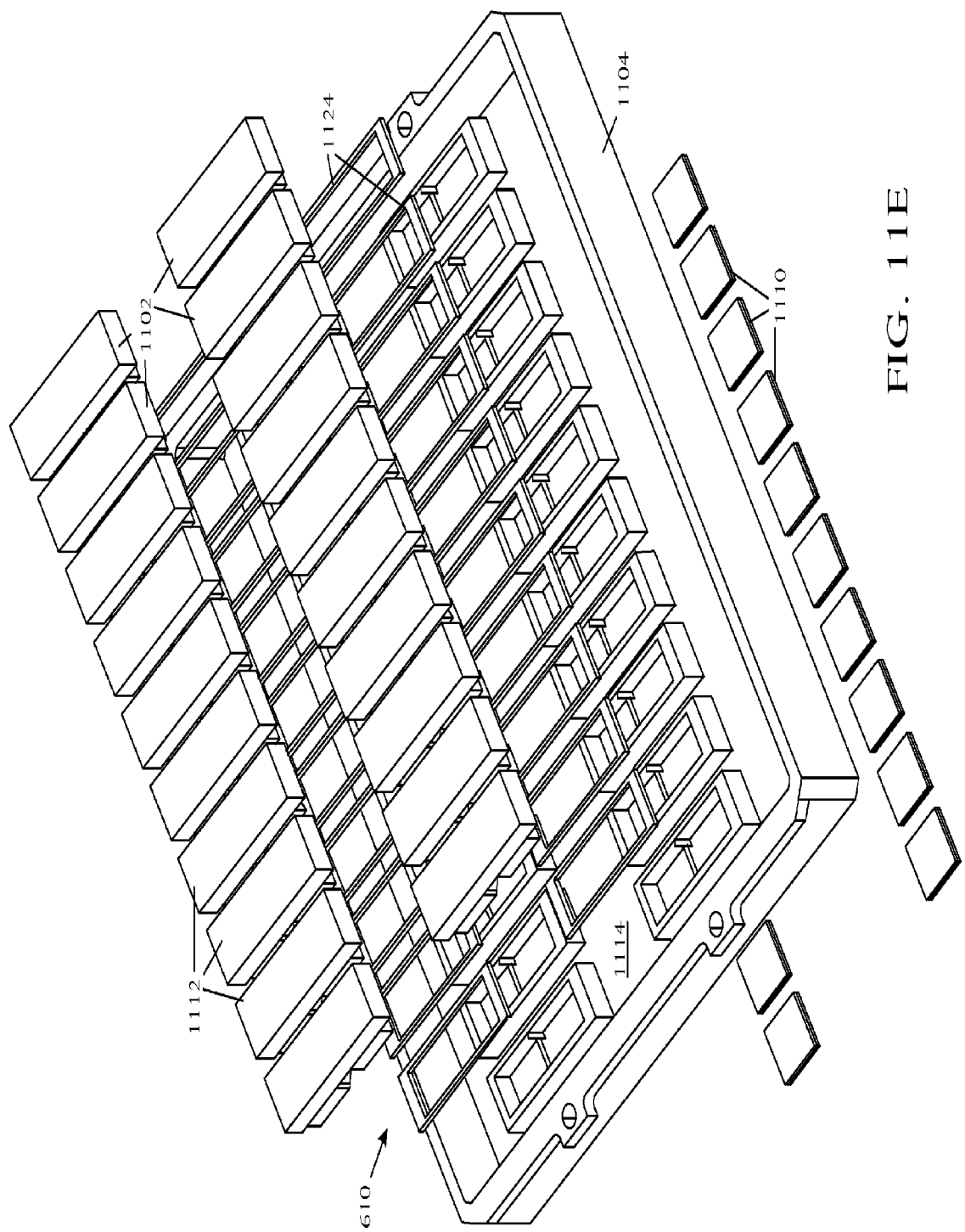
Figure 11F:
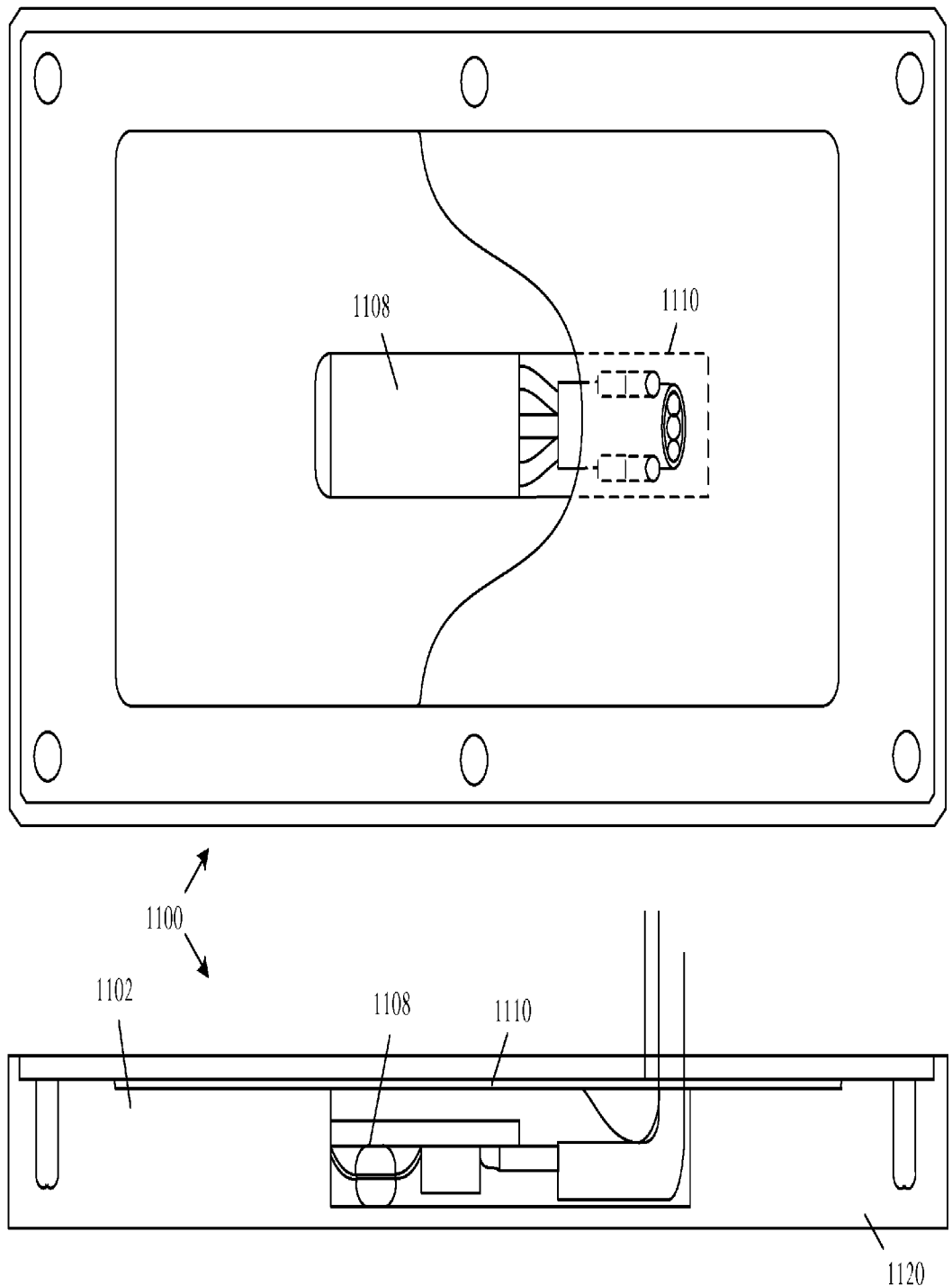
Figure 11G:
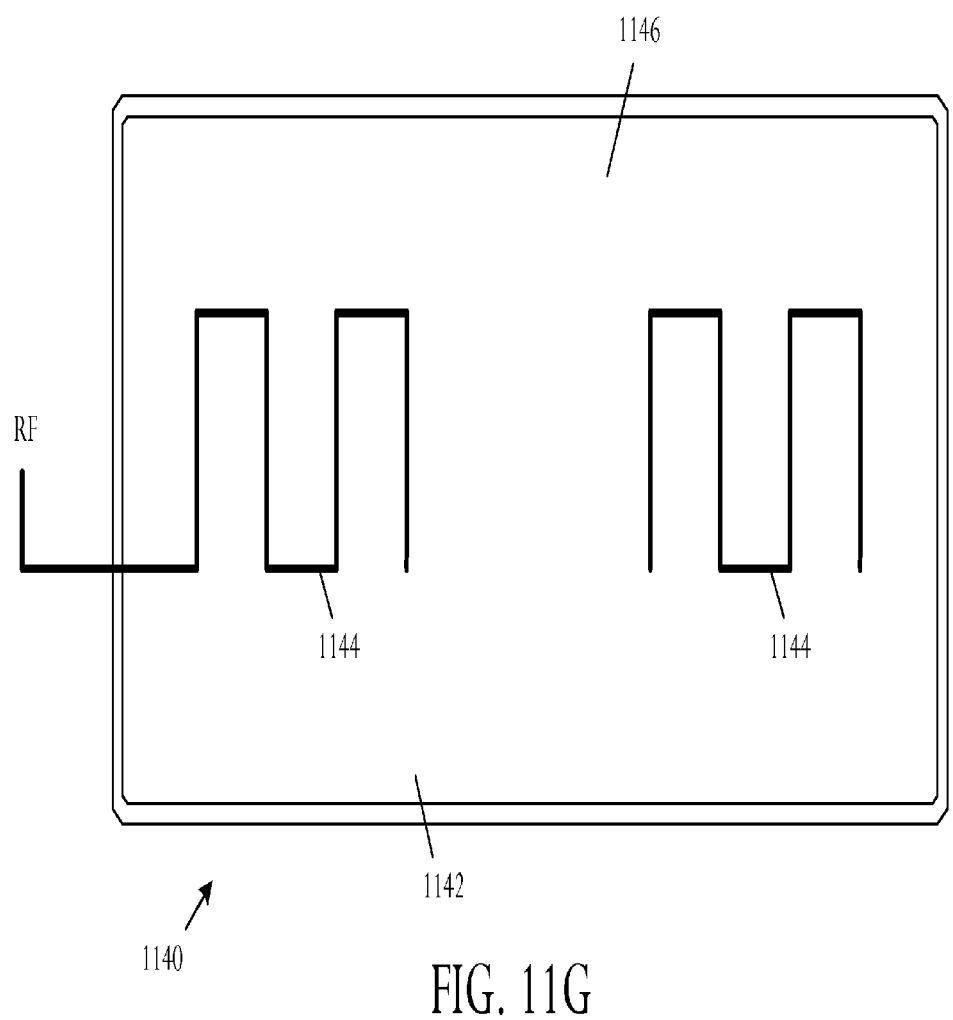
Figure 11H:
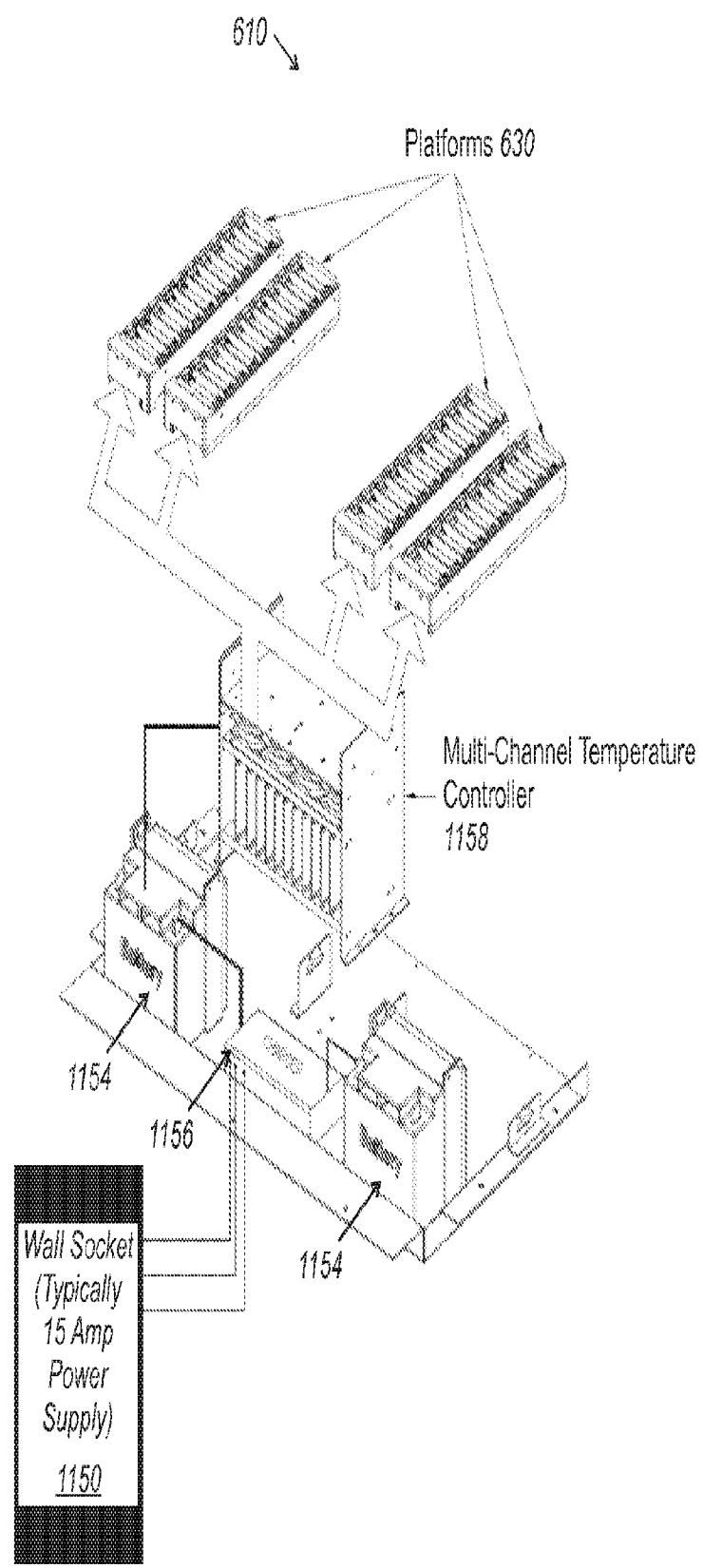

Referring to FIG. 11G, a schematic pictorial diagram illustrates a view of another temperature control element embodiment 1140 that includes piezo-electric mixer or vibrator functionality. A temperature application top 1142 may also include an inter-digital transducer (IDT) 1144 constructed from a material imprinted, embossed, etched, or implanted on the piezo-electric substrate 1146. In some embodiments, the individual temperature control module 1140 for a single position in the temperature control base 1104 may further enable the mixing functionality. The piezo-electric mixer 1148 functions according to surface acoustic wave (SAW) technology so that a radio-frequency (RF) voltage applied to the IDT 1144 creates surface acoustic waves, generating a resonant frequency that can be used to mix contents of a MicroChamber positioned on the temperature control position.

The temperature control base 1104 can be configured as a tray 1114 with peripheral sides forming a fluid containment vessel with drainage aperture 1118. The temperature control base 1104 can be constructed from any suitable material including, for example, temperature and chemical resistant polymers or metals selected from among polypropylene, Kynar™, Teflon™, fluoropolymers, aluminum, and stainless steel. The heat exchanger 1116 is coupled, for example by attachment or integrated, into the base.

The temperature control base 1104 holds multiple temperature control modules 1100. FIG. 11C illustrates a cross-sectional view of a single heating and cooling module 1100. In an illustrative embodiment, the individual temperature control modules 1100 for a single position in the temperature control base 1104 further comprise a base 1120 constructed from a temperature and chemical resistant material, a heat exchanger 1116 integrated into the base plate and constructed from the material of the base 1120, a mount 1122 constructed from a thermally-insulating and chemical-resistant material and coupled to the base 1120, and one or more sealing gaskets 1124 coupled to the mount 1122 and constructed from a temperature and chemical resistant material. The base 1120 is the structural material forming the temperature control base 1104.

The illustrative temperature control modules 1100 further comprise temperature application temperature control elements 1100 constructed from a thermally conductive material and coupled to the temperature control base 1104, a heating/cooling device 1110 secured to the temperature application top 1102; and one or more temperature sensors 1108, for example formed into the temperature application top 1102.

In various embodiments, the heat exchanger 1116 may be in the form and function of cooling fins, liquid coolers, heat sinks, heat exchange coils, cooling loops, heat dissipaters, and others.

FIG. 11D illustrates a perspective view of the temperature control base 1104 and temperature control elements 1100 with temperature application tops 1102 shown elevated from the temperature control assembly 610, exposing for view the sealing gaskets 1124 and heating/cooling devices 1110. FIG. 11E shows a similar perspective view with the temperature application tops 1102, sealing gaskets 1124, and heating/cooling devices 1110 shown at different elevations, exposing the structural form of the temperature control base 1104.

FIG. 11F shows overhead and cross-sectional views of a temperature control element embodiment 1100 that uses a Kapton heating element 1110. A sensor 1108 encapsulated in a sensor cavity with thermally-conductive epoxy. Other embodiments may use elements supporting active cooling.

In a more specific illustrative embodiment, the temperature control assembly 610 may comprise a temperature control base 1104 with multiple temperature control modules 1100. The individual temperature control modules 1100 for a single position in the base 1120 can include a mount 1122, one or more sealing gaskets 1124, a temperature application top 1102, a heating/cooling device 1110, and one or more temperature sensor 1108. The mount 1122 may be constructed from a thermally-insulating and chemical-resistant material such as ceramic, Viton™, Kynar™, PEEK™, and Teflon™. One mount 1122 is included for a heating/cooling element position. The sealing gaskets 1124 are coupled about the mount 1122 and constructed from fluorocarbon rubber, Viton™, or other heat and chemical resistant material. One or more gaskets 1124 may be included for each position. The temperature application top 1102 may overlie the temperature control base 1104 and be constructed from a thermally conductive material such as ceramic, aluminum, brass, copper, or alloy of aluminum, brass, or copper. One temperature application top 1102 is included for a heating/cooling element position. The heating/cooling device 1110 may be a Peltier heating/cooling device, a Thermo-Electric Cooler (TEC), or resistive heater secured to the temperature application top 1102. The temperature sensors 1108 may be integrated circuit (IC) sensors, thermocouples, or thermistor-type temperature sensors sealed into a cavity in the temperature application top 1102. Typically, each position has a single heating/cooling device 1110.

In an illustrative embodiment, heater assemblies contain a thermally-conducting metal plate such as constructed from aluminum, copper, or brass, a temperature sensing device, and a resistive or thermal electric heater. The components are sealed, potted, or molded with a temperature and chemical resistant compound that is also a thermal conductor and electrical insulator. The embodiment may further include a slide carrier and grated barrier slides. The slide carrier can be constructed of an aluminum frame or thermal insulating plastic inserts. The insert reduces thermal cross-talk between slides. The slide carrier and barrier slides can be positioned in the system working space.

Referring to FIGS. 6A-6C In conjunction with FIGS. 11A-11G, the controller 608 is communicatively or controllably coupled to the temperature control assembly 610 and independently sets temperature and controls temperature cycling for individual temperature control elements 1100 and associated substrates and samples of the multiple substrate positions.

The controller 608 manages the sample processing system 600 and the temperature control assembly 610 in combination to independently perform multiple diverse applications simultaneously for individual substrates of the multiple substrates with negligible cross-talk between adjacent substrates. The structure enables independent programming of heating and/or active cooling in individual temperature control modules.

If a large number of slides are to be processed, a run need not be restarted between processing of various batches. Slide racks holding finished slides can be removed and racks holding fresh slides can be introduced during an existing run. Otherwise, slides having higher priority of handling can be introduced into the system without aborting an existing run and can be completed before the slides already being processed.

In accordance with another embodiment of the illustrative system, the controller 608 controls the temperature control assembly 610 for independent control and monitoring of multiple individual channels, corresponding to the multiple temperature control elements 1100. A heating and cooling device 1100 shown in FIGS. 11A-11G is configured to receive a substrate holding a chemical and/or biological sample and the controller 608 controls current magnitude and direction in the heating and cooling devices 1110 using proportional-integrative control based on a first term proportional to error between averaged temperature and a set point and a second term of the error summed over time.

The controller 608 executes a control process that reads a temperature measurement from the heating and cooling device 1100 for the individual channels, samples the temperature measurement with a time constant in a range of hundreds of milliseconds, computes an error term as the difference between the set point and the temperature measurement, and computes the first term and the second term using the error term.

In a particular implementation, temperature is read 200 times per second and stored in a 40-word circular buffer, resulting in a time constant of about 200 milliseconds. Ten times per second, the control process is run and averages the most recent forty temperature readings to obtain temperature T. In other implementations, any suitable sampling frequency and time constant may be used.

The controller 608 can also execute a control process that computes an output response according to equation (1) as follows:

$$\text{Output} = (G^*\text{err}) + (G^*Ki^*\Sigma.\text{err}), \quad (1)$$

where err is equal to set point minus the temperature measurement, Σerr is continuous running sum of the error, Ki is a multiplicative parameter, and G is an overall gain parameter. The output response can be limited to values between a specified positive heating limit and a specified negative cooling limit. The integral Σerr can be set to zero if the first term (G*err) exceeds the largest magnitude of the positive heating limit and the negative heating limit. In some embodiments, overshoot may be reduced by terminating summing of Σerr if either err is greater than a selected windup threshold, or the second term (G*Ki*Σerr) exceeds the largest magnitude of the positive heating limit and the negative heating limit.

In typical operation, at equilibrium, for example with only small error, the integral term predominates. When the set point changes, the proportional term rapidly becomes very large. The temperature approaches the set point only after a response time. During the response time, the integral, if allowed to increase, can become even larger and cause the temperature to drive far past the set point and leading to a large overshoot. To prevent an unstable condition, the integral is zeroed and summing of the integral is terminated while the error is large.

A controller operates the temperature control assembly 610 by issuing several commands including global commands and channel-specific commands. Global commands include a read current command and a power on/off command. Channel-specific commands include: (1) set temperature set point, (2) read temperature, (3) enable/disable output, (4) read all channels, (5) set proportional-integrative (PI) parameters, and read PI parameters.

The read current command returns a measured current consumption in amperes of a heating/cooling device controller. The power on/off command turns on and off a power relay, depending on current status. The power relay controls voltage to the power output section of the heating/cooling device 1110. All functions including temperature readout are operational even when the power relay is in the off setting since only output power is disabled.

The set temperature set point command sets a target temperature for a channel. If the power relay is on, then channel output is enabled and the controller attempts to attain and maintain the set point temperature. Read temperature returns a single channel temperature readout. Enable/disable output performs the operation of enabling or disabling the channel output. In the disabled state, the temperature readout remains active and the set point may be changed, but no current flows through the heating/cooling device 1110. In the disabled state, the temperature does not regulate. The read all channels command reads all channels at one time, returning a large packet containing either temperature or set point data along with channel status flags for each channel. Read PI parameters reads back any requested PI control algorithm parameter. Set PI parameters sets the PI control algorithm parameter to the specified value. The parameters include overall proportional term gain (G), an integrative term multiplicative factor (Ki), windup threshold (W), positive threshold (M+), negative threshold (M−), and set point (SP).

Figure 12:
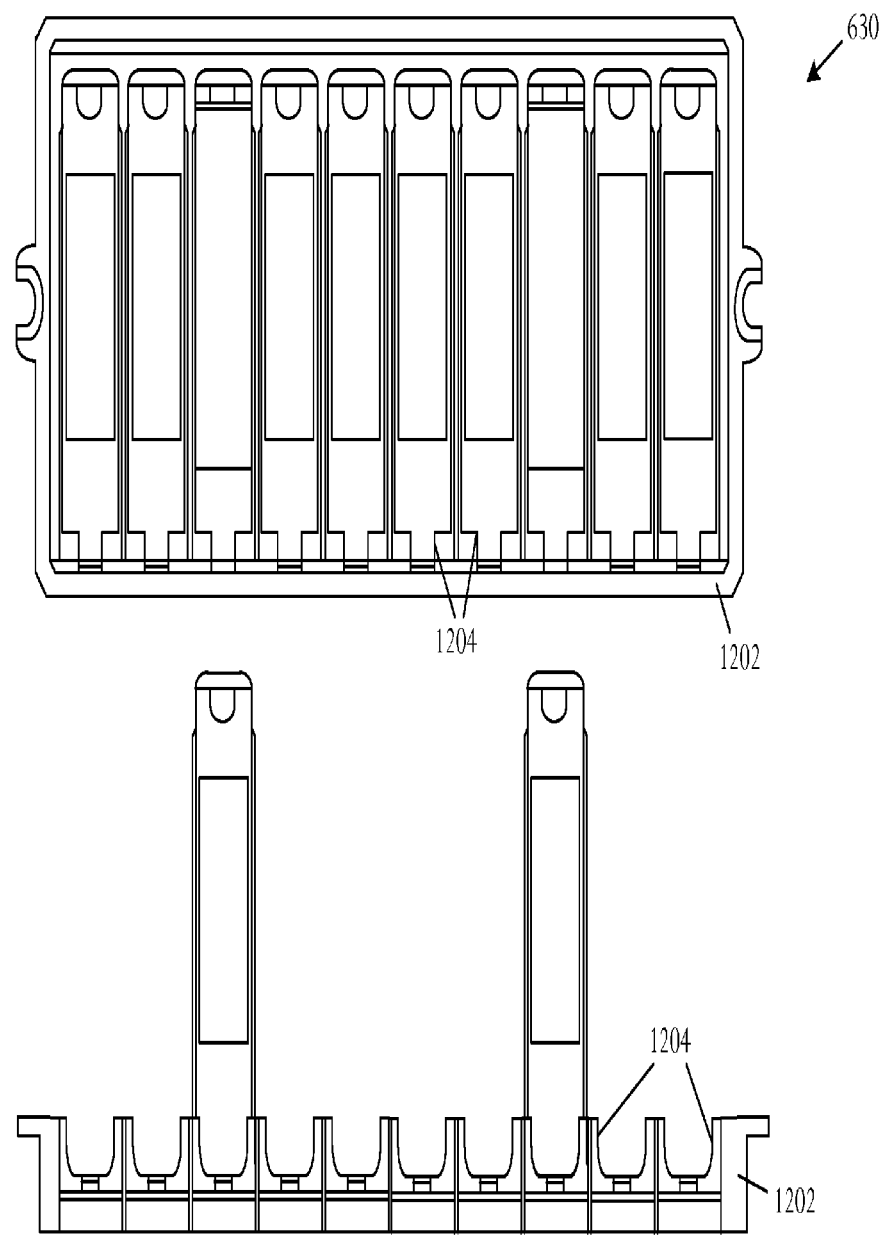
FIG. 12 shows an embodiment of a platform comprising a carrier frame and a plurality of inserts that reduce thermal cross-talk between the substrates of FIGS. 6A-6E.

Referring to FIG. 12, a pictorial diagram illustrates an embodiment of the platform 630, comprising a carrier frame 1202 and a plurality of inserts 1204 that reduce thermal cross-talk between the substrates. The carrier frame 1202 is constructed from a material, such as aluminum, and the inserts 1204 are constructed from aluminum or thermal-insulating plastic.

The substrate or slide carrier enables multiple substrates, for example ten slides, to be placed together onto the substrate positions while holding the substrates in contact with temperature application tops, and prevent the substrates from being pulled out of the carrier during removal of the Micro-Chamber covers. The platform is generally constructed of materials that reduce or minimize thermal convection for more efficient temperature control.

Referring again to FIGS. 6A-6C, some embodiments of the sample processing system 600 can also include one or more mixers 612 adapted to mix the contents of the MicroChambers 602 collectively, and/or individually. The controller 608, or other suitable mixing control device, can be coupled to control operation of the mixer(s) 612. An environment mixing system 658 may be implemented in the sample processing system 600. The environment mixing system 658 comprises the sample processing system 600 configured to mix an environment within a MicroChamber 602.

In some embodiments, a vibration motor 660 can be included that is positionable in the vicinity of the Micro-Chamber 602. The controller 608 is communicatively coupled to the vibration motor 660 and adapted to generate a vibration in the MicroChamber 602.

In other embodiments, the robotic device 640 is adapted to move relative to the MicroChamber 602 and a member, for example one or more cushioned members, needles, pens, pipettes, or other items attached to the pipette tip handling device 652 is attached to the robotic device 640. The controller 608 controls the robotic device 640 to a position to generate a vibration in the MicroChamber 602. For example, the MicroChamber cover(s) can simply be touched once or repeatedly to send a pressure pulse through the microenvironment.

In further embodiments, a piezo-electric transducer 662 can be included that is positionable in the vicinity of the MicroChamber 602. The controller 608 is communicatively connected to the piezo-electric transducer 662 and adapted to generate a vibration in the MicroChamber 602.

In other embodiments, the temperature control assembly 610 has active heating and cooling capability and is positionable in the substrate vicinity. The controller 608 controls the temperature control assembly 610 and programmed to generate a motion in the microenvironment by temperature cycling.

Other suitable vibration techniques and devices can be utilized to mix the contents of the MicroChamber(s) 602.

The sample processing system 600 in FIGS. 6A and 6B is shown without an enclosure to enable viewing of a robotic device 640 and other internal components, devices, and parts. FIG. 6C shows an enclosure 664 around components on the platform 630 of the sample processing system 600. The enclosure 664 can be fabricated with transparent material to allow an operator to view operation of the processing system 600. The enclosure 664 can also help protect the MicroChambers 602 from contamination, as well as help control the microenvironment of the MicroChambers 602.

A tip disposal orifice 622 can be included in some embodiments of the sample processing system 600 to allow the robotic head 640 to discard used pipette tips 626. A tip disposal bin 624 can be located adjacent the tip disposal orifice 622 to store discarded pipette tips 626. A horizontal bar 628 can be located at the center of the tip disposal orifice 622 to help prevent discarded pipette tips 626 from stacking and blocking the disposal orifice 622. A drain bin 632 can be positioned under the platform 630 for draining fluids to a waste container.

A pipette tip holder can also be included in some embodiments of the sample processing system 600 and configured with one or more pipette tip racks 634A and 634B capable of containing arrays of pipette tips 626. A reagent vial holder 636 is shown adjacent the pipette tip racks 634A and 634B and can be affixed to the platform 630 or adapted to be removable from the platform 630.

A slide holder 629 can also be included in some embodiments of the sample processing system 600 to hold one or more substrates or slides for future use. Another slide holder can be included to store used substrates or slides.

Figure 13:
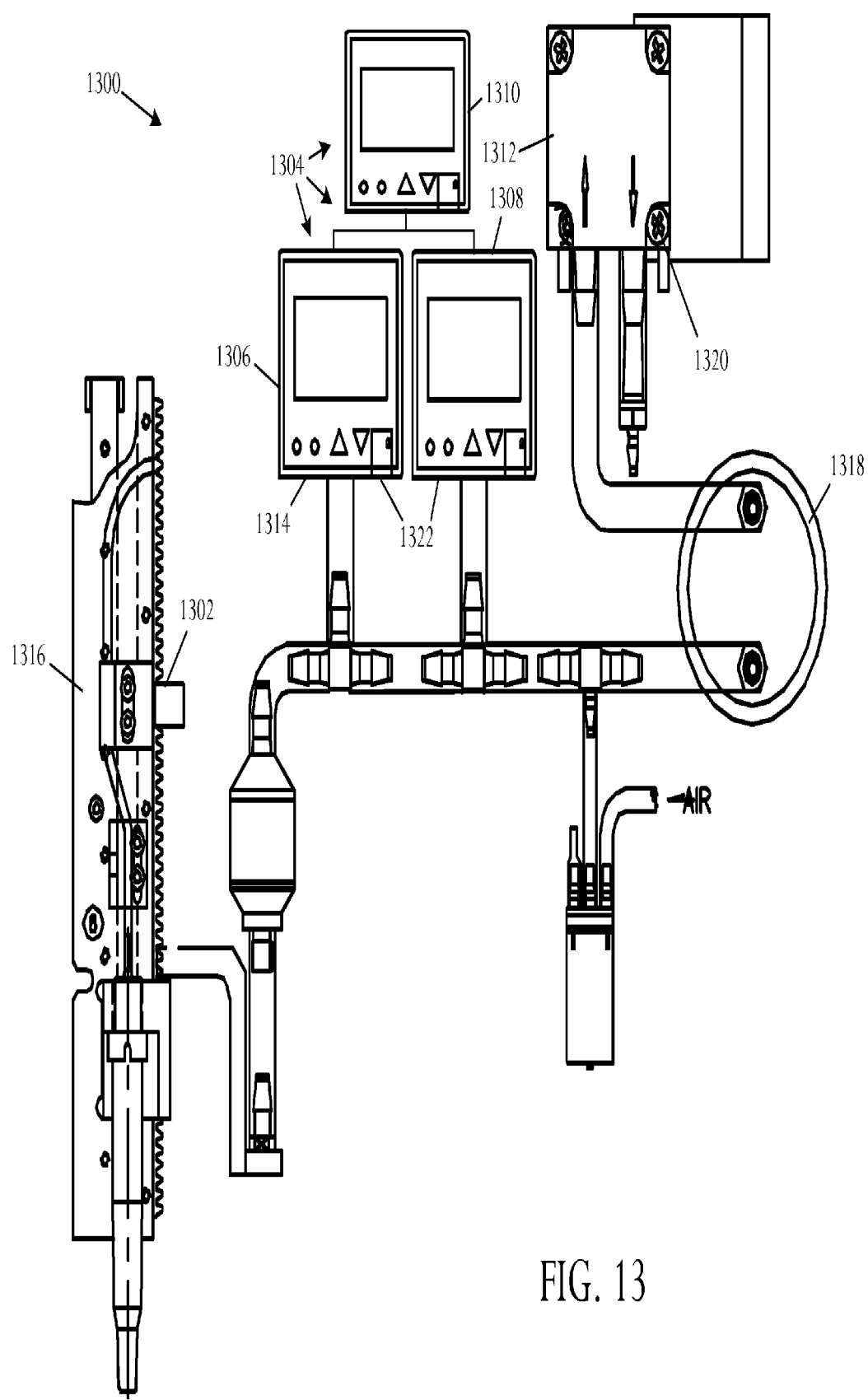
FIG. 13 shows an embodiment of a fluid handler for usage in the sample processing system of FIGS. 6A-6E.

Referring to FIG. 13, a schematic pictorial diagram illustrates an embodiment of a fluid handler 1300 for usage in a sample processing system. The fluid handler 1300 comprises a fluid dispenser 1302 and a fluid level detector 1304. The fluid dispenser 1302 is operative in a system for handling chemical and/or biological samples. The fluid dispenser 1302 is adapted to dispense one or more selected fluids to a selected sample. The fluid level detector 1304 comprises a combined vacuum detector 1306 and pressure detector 1308. The liquid level of a reagent can be sensed using the vacuum system to avoid creation of bubbles in the reagent, thereby introducing sensing uncertainty in the fluid level.

The fluid dispenser 1302 can further comprise a controller 1310 that communicates with the fluid level detector 1304 and is adapted to selectively operate the vacuum detector 1306 to measure fluid level for relatively large volume, low viscosity fluids. Similarly, the controller 1304 selectively operates the pressure detector 1308 to measure fluid level for relatively low volume and high viscosity fluids.

The fluid handler 1300 further comprises a metering pump 1312 that is cycled to create a vacuum source, a vacuum switch 1314 for detecting a pressure change, and the controller 1310 that is adapted to receive a signal indicative of the change in pressure. The fluid handler 1300 can further comprise a robotic handler 1316 adapted to manipulate a pipette including a pipette tip. The controller 1310 executes a control operation that includes lowering the pipette into a fluid container, receiving a signal from the vacuum switch 1314 upon detection of the pressure change when the pipette tip touches the fluid surface in the container, saving pipette position information at the pressure change, and determining the distance to move the pipette to aspirate a selected fluid volume.

The pressure detector 1308 also uses the metering pump 1312 and controller 1310 along with a pressure switch 1318 that determines a positive pressure on detection of a pressure change. The controller 1310 receives a signal indicative of the pressure to determine fluid level. The controller 1310 executes a control operation that includes lowering the pipette into a fluid container, receiving a signal from the pressure switch 1318 indicative of positive pressure to determine when the pipette tip touches or nearly touches the fluid surface in the container, saving pipette position information at the pressure change, and determining the distance to move the pipette to aspirate a selected fluid volume.

The fluid handler 1300 can also include the sample processing system which is adapted to dispense at least one reagent fluid to a chemical and/or biological sample. One or more reagent/probe containers contain fluids to be dispensed during sample handling. The fluid dispenser 1302 and fluid level detector 1304 can be used to determine fluid level in the reagent/probe containers.

The controller 1310 can mange the fluid level detector 1304 to select between operation of the vacuum detector 1306 and the pressure detector 1308 to reduce or eliminate bubbles in the liquid. For example, usage of the vacuum detector 1306 reduces formation of bubbles for relatively large volume, low viscosity fluids.

According to another embodiment of the fluid handler 1300, the sample processing system is adapted to apply at least one selected reagent to a chemical and/or biological sample in an automated process. The sample processing system includes one or more reagent/probe containers. A vacuum and pressure source 1320 is coupled to the sample processing system and used to dispense fluids. A vacuum and pressure sensor 1322 is coupled to the sample processing system and used to measure a condition of the reagent/probe containers. The fluid level detector 1304 operates in conjunction with the vacuum and pressure source 1320, vacuum and pressure sensor 1322, and fluid level detector 1304 and detects fluid level in the reagent/probe containers selectively based on either vacuum or pressure changes.

Figure 14:
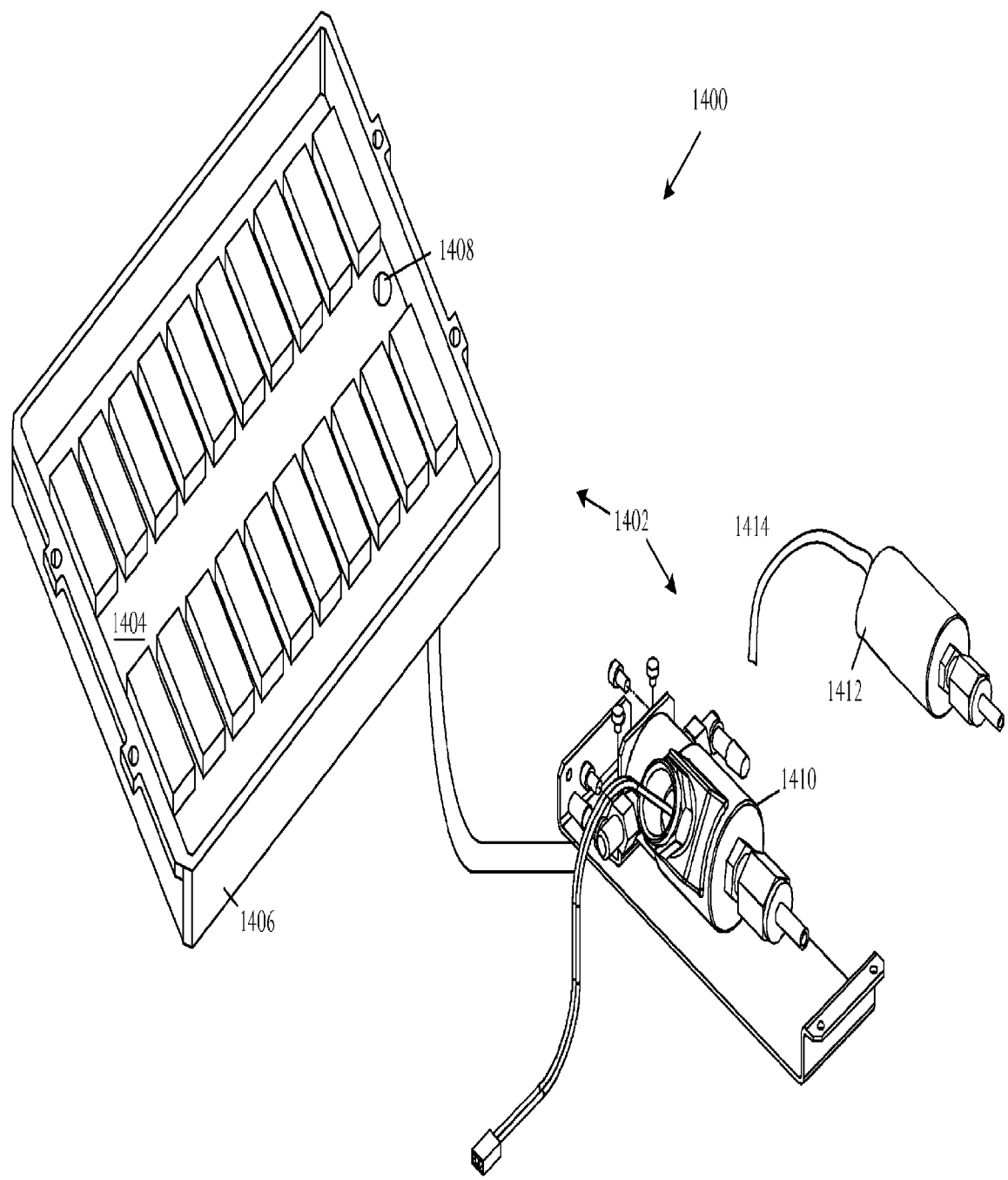
FIG. 14 shows an embodiment of a temperature control base coupled to a plurality of individual substrate temperature control assemblies and a waste drain tray coupled to the temperature control base.
Figure 15:
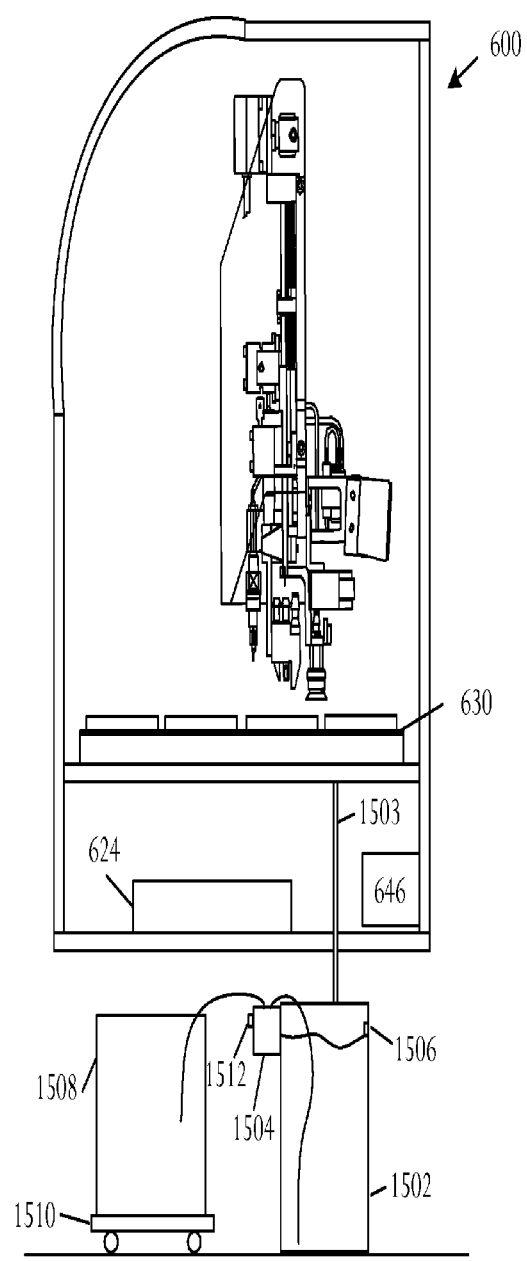
FIG. 15 shows an embodiment of a waste handling system that can be used in the sample processing system of FIGS. 6A-6E.

A toxic reagent in a process can become a waste product. Toxic waste can be separated from non-toxic waste to reduce the volume of toxic waste for disposal. Referring to FIG. 14, a schematic pictorial diagram illustrates an embodiment of a waste handling system 1400 that can be used in a sample processing system. The waste handling system 1400 comprises a sample processing system configured to apply at least one selected reagent to a chemical and/or biological sample on a substrate in an automated process and a waste separation system 1402. The waste separation system 1402 is adapted to divert effluent waste from the sample processing system into a plurality of separate parts under program control.

The waste separation system 1402 comprises a platform 630, a waste drain tray 1406 coupled to the platform 630 and having an outlet 1408, a multiple-way diverter valve 1410 coupled to the waste drain tray outlet 1408, a pump 1412, and drain lines 1414. The pump 1412 programmably separates the effluent.

A controller can be coupled to the sample processing system, the multiple-way valve 1410, and the pump 1412 and can be adapted to programmably automate application of reagent dispensing and separation of effluent in a combined operation. Based on chemicals specified by a protocol, the controller switches the diverter valve 1410 directing waste to hazardous or nonhazardous waste receptacles. The pump 1412 assists waste flow to the receptacles. The controller can perform automatic separation of toxic from non-toxic waste in combination with control over other operations on the sample, such as dispensing of reagents and washing. The controller redirects fluid by switching the valve 1410, for example using software commands. For example, the controller can control dispensing of the reagents based on information relating to toxicity of the particular reagents. For known toxic reagents, the controller can control the multiple-way valve 1410 to direct the fluid to a toxic disposal container. Similarly, for non-toxic reagents, the controller manages the multiple-way valve to direct the effluent to a non-toxic disposal container. In another application, the controller can automate application of multiple reagents to samples and separation of multiple waste effluents into different effluent waste receptacles in a combined operation.

In some embodiments, the waste handling system 1400 can include a platform 630 that further includes, referring to FIGS. 11A-11G in combination with FIG. 14, a temperature control base 1104 coupled to a plurality of individual substrate temperature control assemblies 1100, and a waste drain tray 1114 coupled to the temperature control temperature control base 1104. The waste drain tray 1114 has an outlet or drain 1118. The multiple-way valve 1410 is connected to the waste drain tray outlet 1118 and can be programmed to controllably separate the effluent by gravity flow.

The components in the sample processing system 600 can be arranged in specified locations and orientations relative to the robotic arm 640. The configuration of the components can be specified by a user via a user interface, or may be pre-programmed. Knowledge of the location and orientation of the components allows more accurate and efficient operation of the robotic head 640. Additionally, configuration of the sample processing system 600 can be adapted for particular processes or protocols to be performed. For example, the operator can customize the configuration to accommodate specified sizes and numbers of covers, pipettes, MicroChambers 602, and reagents, among others.

Additionally, in some embodiments, the components in the sample processing system 600 can include features such as an encoder or RFID tag that allows the identity of the components, the position of the components on platform 630, and other characterizing information about components to be determined without requiring the information to be preprogrammed or input by the operator. The controller 608 can use the information to accurately position and operate the robotic device 640 relative to the other components in the sample processing system 600.

Further, components in the sample processing system 600 can include bar codes, an RFID tag, or other identifier than can be detected by sensors and/or signal receivers in or near the sample processing system 600. The controller 608 or other suitable computer processing device can include logic that allows the location of the components to be tracked and recorded. For example, a reagent container 644 may be taken from one sample processing system 600 and installed in another sample processing system 600. If the component, such as the reagent container 644, includes an identifier, the controller 608 can identify the component and provide information regarding the new location of the component to an operator. Additionally, the system 600 from which the component was removed can detect the event and can issue a suitable alert, such as a text or voice message to the operator, when a process is selected that requires replacement of the component.

Two or more of the sample processing systems 600 can be coupled to a network to provide and receive information from each other. Information from each system 600 can be collected, and logs and statistics regarding the operation of one or more of the systems 600 can be provided from each processing system 600 and/or from any other system configured to communicate with the network of systems 600. Any suitable communication interfaces and protocols can be utilized to form a network of the systems 600.

The robotic device 640 can be moved to different locations over the platform 630 by the action of motors that operate in combination with sliding tracks to precisely position the robotic device 640 at a specified location. An X-axis track 638 is shown as the principal lengthwise horizontal axis of the apparatus. A single X-axis track 638 is supported at either end on bearing shafts and brackets. A Y-axis track 664 allows movement of the robotic head 640 in a second dimension. Movement of the tracks 638, 664 is enabled by motors operated by a controller, computer, or other suitable device. The Z-axis is orthogonal to the X and Y axes. Additional X-axis tracks 638 and Y-axis tracks 664, or other suitable structure can be included in the sample processing system 600 to allow one or more additional robotic devices 640 to move independently of one another and reduce the amount of time required to process multiple chambers 602.

Flexible electronic leads and tubing, including both gas and liquid supply conduits, can lead from the robotic device 640 to appropriate fluid reservoirs and/or electronic control equipment. The supply conduits are suitably long, flexible and durable and can originate from various pumps. The supply conduits can pass through a flexible wire carrier on one side of X-axis track 638, and through a wire carrier at the top of the X-axis track 638 to conduct supply conduits to movable arm 614 and robotic device 640.

In an illustrative system, power can be supplied to the sample processing system 600 by alternating current (AC) to direct current (DC) medical-grade power supplies. Most functions, other than high-power operations such as compressor and blower functionality, can operate on low voltage DC power. In a typical embodiment, an air compressor may supply a linear, regulated range of 3-6 pounds per square inch (PSI) or other suitable pressure, with a blower with linear control, open 0.7 cubic feet per minute (CFM), and a vacuum with open condition of 450-0 mm/Hg. Any other suitable compressor, blower, and vacuum specification may be implemented.

In some embodiments, the robotic device 640 may include a closed-loop or open-loop motion controller that uses a Proportional Integral Differential (PID) or Proportional-Integrative algorithm, and or other process control algorithms to perform motion control. In some embodiments, the robotic device 640 can be positioned with accuracy in the X and Y axes to 0.2 mm, and positional accuracy in the Z-axis to 0.4 mm, however, the processing system 600 can be configured with components that achieve other levels of accuracy.

Motors or other suitable drive components move the movable arm 614 under computer control, enabling programming of arm movement between various work locations on the platform 630. The robotic device 640, which can include a hollow tip head to dispense liquids or gasses through the robotic device 640 to the MicroChambers 602. In some embodiments, the movable arm 614 is configured with either multiple, permanently attached tips with different functions or multiple disposable tips located on the movable arm 614 concurrently. For example, a single hollow channel in the robotic device 640 may have multiple channels connected to separate pumps with individual tips having possibly different functionality attached. A portion of the robotic device 640 can be adapted to pick up pipette tips 626 from the standard tip racks 634A, 634B. The pipette tips 626 can be oriented in the tip racks 634A, 634B to allow the tip handling device 652 to engage the base of the tips 626 for insertion onto the robotic device 640. The tips 626 can be arranged in an array so individual tips 626 in the racks 634A, 634B are accessible to the user and the robotic device 640.

In some embodiments, the pipette tip handling device 652 can use two different sizes of pipette tips interchangeably by virtue of usage of a tip adapter having a two-taper design. The design enables the tip adapter to pick up more than one pipette tip size, enabling precision dispensing in a range from 0.1 nanoliters (nl) to 1000 µl or more. The tip adapter can have multiple tapers to fit different size tip barrels. A sensor or other suitable device can be used to determine contact with a pipette tip 626. The level of substance remaining can be used to check the accuracy of countdown volume for the particular container 644.

The movable arm 614 can be controlled to move to a particular predetermined location and carry out a pre-selected motion or other operation, such as grasping or releasing a tip 626 from the robotic device 640. Standardized motions of the arm 614 can be programmed so that individual MicroChambers 602 at specific predetermined locations on the platform 630 can be treated with reagents and/or wash fluids obtained from reagent containers 644 or other substances supplied through the robotic device 640. The amount of reagent or other substances used can be tracked as inventory information that can be shared among networked processing systems 600 and accessed by operators.

During operation multiple MicroChambers 602 are placed in a tray that is inserted at a predetermined location, usually according to registration pins in the tray so that individual MicroChambers 602 are always located in the predetermined relative positions on the platform 630. The sample processing system 600 is programmed appropriately for operation with components placed at predetermined or determinable locations.

The robotic device 640 can also be configured with a wash head 654 and a blow head 656. The wash head 654 is capable of delivering one or more different bulk solutions in any volume selected by a process. The robotic device 640 can apply liquid to a MicroChamber 602 from a wash buffer reservoir via a liquid supply conduit to the wash head 654. The blow head 656 can be used to remove excess buffer from the MicroChamber 602 prior to subsequent processing. Removal can be performed by blowing gas through the blow head 656 while the robotic device 640 travels along the X, Y, and/or Z axes without disrupting the contents of the MicroChamber 602. A small amount of buffer can be left on the MicroChamber 602 to assist in reagent distribution.

In some embodiments, the wash head 654 can dispense fluid in a range from 35 μl to 610 μl. In other embodiments, any suitable fluid volume may be dispensed. The wash head 654 may be constructed from any suitable material such as acrylic and/or stainless steel and can be mounted on a linear slide to enable back and forth washing motion.

The robotic device 640 can be controlled to engage a pipette tip 626 from the pipette tip racks 634A, 634B, move the pipette tip 626 to a selected reagent container 644, and draw a selected amount of reagent using vacuum suction. The sample processing system 600 can be programmed for efficient operation to deliver the particular reagent to multiple specimens that are to be treated with the reagent. The robotic device 640 can be moved to the appropriate specimens to dispense the reagent in a pre-assigned pattern that operates in combination with a thin liquid film on the MicroChamber 602 to assure spreading of the reagent over the entire surface of the MicroChamber 602.

The disposable pipette tip 626 can then be discarded and the movable arm 614 moves the wash and blow heads to apply buffer and then remove excess buffer from the next group of MicroChambers 602 to be processed, while the prior group of MicroChambers 602 are incubated with the reagent. The robotic device 640 can engage the next available disposable tip from the tip rack and a selected reagent can be drawn into the tip and applied. Selected steps can be repeated until all specified MicroChambers 602 are treated with reagent or reagent incubation is complete and reagents may be removed.

In some implementations, the controller 608 can be integrated with other processing components in the sample processing system 600, or in a stand-alone computer, for example running a common operating system such as Windows NT™, 2000™, XP™, or others. In a typical implementation, the controller 608 can run multiple, different, protocols simultaneously. For example, in some embodiments staining can be implemented in a possible platform of forty slides, thirty bottle reagents, and ninety-six well-plate reagents. Any suitable configuration may be implemented. The controller 608 can enable either open runs or barcode runs. Built-in factory protocols may be implemented as well as user-defined or custom protocols.

The controller 608 can generate a user interface that allows an operator to preview an entire protocol and edit selected portions of the protocol before starting the process. A slide map may be displayed showing real-timer protocols, processing, and progress. The system can display run-time and time to completion. Details of current operation can be displayed in a status box. The system 600 can support print reports for slide workload, reagent workload, missing reagents in a barcode run, insufficient reagents in a barcode run, expired reagents in a barcode run, assay reports, run logs, and the like.

In some embodiments, the controller 608 may enable set-up of subsequent open runs only during a current run. Reagent volume countdown may be performed for a run and/or a series of runs. Audio and visual alarm features may be included for protocol run completion and system errors. The system 600 may support pause and stop function icons on various or all graphical user interface displays. Safety confirmation may be displayed when deleting slides. The system may support a virtually unlimited number of protocol steps. The system may support optimization of priming location for the robotic device 640 and keyboard functions to move the robotic device 640 during calibration. A save function may be implemented for the calibration procedure.

A single-user login may be supported. A drop-down list box may be displayed for multiple specimen types and user names. A user-defined reagent dispensing pattern may be supported on a substrate during a run.

In some embodiments, the system 600 can search for subsequent pipette tips if a tip is missing. A start/cancel delayed start function can be implemented after programming a protocol. The system 600 can enable editing of single slides in the barcode and open formats, and may enable multiple edits in the barcode and open formats. The system 600 can support a capability to buffer slides before and after runs. The system 600 may further support an error message history file and a protocol control-login requirement for particular defined protocol modifications.

Various features of the system 600 enable aspects of walk-away automation. For example, the controller 608 can use a STAT feature that allows the operator to prioritize processing of one or more selected samples.

Similarly, the controller 608 can enable a continuous access capability including a capability to remove a finished sample or a sample in the middle of a run and replace the sample with another while processing of other samples continues.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. For example, although particular systems are described that include many novel features, each of the different features may be implemented in a system that either includes or excludes other features while utility is maintained.

In the claims, unless otherwise indicated the article "a" is to refer to "one or more than one".

The invention claimed is:

1. An apparatus comprising:
a sample processing system (600) adapted to concurrently and individually control processing of a plurality of samples within a plurality of microchambers formed on a corresponding plurality of substrates, wherein the system comprises:
 a cover handling device (606) adapted to position individual covers on each of the substrates to enclose each sample and form a microchamber;
 a substance dispensing device (604), adapted to dispense one or more substances in the microchamber in a range from 0.1nl to 1000 µl;
 a temperature control assembly (610) having an array of individually controlled temperature control elements (1100), the temperature control assembly (610) being adapted to heat and cool individual microchambers on the plurality of substrates independently during a temperature cycle; and
 a controller (608) coupled to the cover handling device (606), substance dispensing device (604) and temperature control assembly (610), adapted to concurrently and independently control the micro-environment within each microchamber on the plurality of substrates,
 wherein the microchamber comprises a cover, a reservoir formed on the substrate for receiving at least a portion of one of the plurality of samples and a vesicle coupled to the cover and containing a substance to be dispensed on the sample.

2. The apparatus according to claim 1, wherein:
the controller (608) being adapted to programmably control the micro-environment of the samples by selectively executing a sequence of actions selected from among actions of placing a cover over the sample, removing the cover, dispensing a selected reagent on the sample; and washing the sample.

3. The apparatus according to claim 1, wherein:
the controller (608) coupled to the temperature control assembly, being adapted to programmably heat and cool the samples.

4. The apparatus according to claim 1 further comprising:
a mixer (612) configured to mix substances on the substrates; and the controller (608) coupled to the mixer and adapted to operate the mixer.

5. The apparatus according to claim 2 further comprising:
a cover dispenser (802) that individually dispenses at least one cover, the dispenser being capable of dispensing covers of multiple different sizes;
a robotic head (804) adapted to move relative to the cover dispenser and the substrates; an effector (806) coupled to the robotic head that programmably grips and releases the covers, the effector being operable to perform multiple functions including removing covers from the cover dispenser, moving the covers to a specified position, placing one of the covers on one of the substrates, and removing the cover from the substrate.

6. The apparatus according to claim 5 wherein:
the effector (806) further comprises one of the group consisting of:
at least one vacuum pad that grips and releases the covers, an electromagnetic attachment device that grips and releases the covers, and a mechanical robotic attachment device that grips and releases the covers.

7. The apparatus according to claim 1 further comprising:
a sealing assembly (650) further comprising a sealant pen, a sealant reservoir coupled to the sealant pen, a sealant valve controller, and a sealant pen valve that is manipulated by the robotic head to selectively eject a pattern of sealant to create a chamber around a least a portion of the sample on the substrate.

8. The apparatus according to claim 1 further comprising:
a program code executable on the controller and configured to determine type, size, and/or location of the sample on the substrate.

9. The apparatus according to claim 1 further comprising:
a liquid dispenser (1002) that dispenses liquid on the sample on a substrate in a selected volume range including a capability to consistently dispense a selected liquid in volumes as low as 0.1 ul; and
a pipette tip handling device (1004) coupled to the liquid dispenser that aspirates and dispenses a micro-volume of the selected liquid via a pipette tip selected from among a plurality of different sized pipette tips.

10. The apparatus according to claim 9 further comprising:
a wash head (1006) coupled to the pipette tip handling device and configured to deliver a plurality of selected bulk solutions in a plurality of controlled volumes to sample on the substrate; and
a blow head (1008) configured to remove excess liquid from the sample.

11. The apparatus according to claim 1 further comprising:
a sealant pen configured to dispense a selected amount of sealant in a programmed pattern on the substrate around at least a portion of the sample.

12. The apparatus according to claim 1 further comprising:
a substrate carrier(1202) comprising a carrier frame that reduces thermal cross-talk between the substrates.

13. The apparatus according to claim 4 wherein:
the mixer (612) is at least one of the group consisting of:
 a mechanical oscillator, an electric oscillator, a piezoelectric element, an ultrasonic pulse device, a device that produces oscillation based on application of temperature cycling, and an inter-digital transducer (IDT).

14. The apparatus according to claim 1 further comprising:
a plurality of reagent/probe containers;
a vacuum and pressure source (1320) operable to dispense fluids; a vacuum and pressure sensor (1322) operable to measure a condition of the reagent/probe containers; and
a fluid level detector (1304) operable to detect fluid level in the reagent/probe containers selectively based on either vacuum or pressure changes.

* * * * *

UNITED STATES PATENT AND TRADEMARK OFFICE
CERTIFICATE OF CORRECTION

| | | |
|---|---|---|
| PATENT NO. | : 8,968,675 B2 | Page 1 of 1 |
| APPLICATION NO. | : 13/926216 | |
| DATED | : March 3, 2015 | |
| INVENTOR(S) | : Krishan L. Kalra | |

It is certified that error appears in the above-identified patent and that said Letters Patent is hereby corrected as shown below:

In the specification

In column 2 at line 27, Change "FIGS. 6A-6E; and" to --FIGS. 6A-6E;--.

In column 2 at line 31, Change "base." to --base; and--.

In column 9 at line 62, Change "0.1 ul to 1000 ul" to --0.1 μl to 1000 μl--.

In column 11 at line 21, Change "active active" to --active--.

In column 18 at line 8, Change "mange" to --manage--.

In column 20 at line 34, Change "and or" to --and/or--.

In the claims

In column 24 at line 16, In Claim 7, change "a least" to --at least--.

In column 24 at line 26, In Claim 9, change "0.1 ul;" to --0.1 μl;--.

In column 24 at line 43, In Claim 12, change "carrier(1202)" to --carrier (1202)--.

Signed and Sealed this
Twenty-second Day of December, 2015

Michelle K. Lee
*Director of the United States Patent and Trademark Office*